US010667797B2

(12) United States Patent
Bladen et al.

(10) Patent No.: US 10,667,797 B2
(45) Date of Patent: Jun. 2, 2020

(54) TISSUE SAMPLING

(71) Applicant: SNPSHOT TRUSTEE LIMITED, Auckland (NZ)

(72) Inventors: Roy Victor Bladen, Auckland (NZ); Michael Stuart Gardner, Auckland (NZ)

(73) Assignee: SNPSHOT TRUSTEE LIMITED, Auckland (NZ)

( * ) Notice: Subject to any disclaimer, the term of this patent is extended or adjusted under 35 U.S.C. 154(b) by 672 days.

(21) Appl. No.: 14/896,322

(22) PCT Filed: Jun. 5, 2014

(86) PCT No.: PCT/NZ2014/000107
§ 371 (c)(1),
(2) Date: Dec. 4, 2015

(87) PCT Pub. No.: WO2014/196877
PCT Pub. Date: Dec. 11, 2014

(65) Prior Publication Data
US 2016/0128677 A1 May 12, 2016

(30) Foreign Application Priority Data

Jun. 5, 2013 (NZ) ........................................ 611547
Oct. 18, 2013 (NZ) ........................................ 616807

(51) Int. Cl.
*A61B 10/02* (2006.01)
*A01K 11/00* (2006.01)
(Continued)

(52) U.S. Cl.
CPC ........ *A61B 10/0233* (2013.01); *A01K 11/002* (2013.01); *A01K 11/003* (2013.01);
(Continued)

(58) Field of Classification Search
CPC .................................................. A01K 11/003; A01K 11/002; A61B 10/0096; A61B 10/0266
See application file for complete search history.

(56) References Cited

U.S. PATENT DOCUMENTS 4,976,925 A 12/1990 Porcher
5,810,806 A 9/1998 Richart et al.
(Continued)

FOREIGN PATENT DOCUMENTS

AU 2009329486 11/2014
CN 1275894 12/2000
(Continued)

OTHER PUBLICATIONS

International Search Report and Written Opinion from the International Searching Authority for Application No. PCT/IB2014/065394 dated Feb. 9, 2015 (9 pages).
International Preliminary Report on Patentability for Application No. PCT/IB2014/065394 dated Feb. 3, 2016 (4 pages).
International Search Report and Written Opinion from the International Searching Authority for Application No. PCT/IB2014/065395 dated Feb. 10, 2015 (12 pages).
(Continued)

*Primary Examiner* — Patrick Fernandes
(74) *Attorney, Agent, or Firm* — Michael Best & Friedrich LLP

(57) ABSTRACT

The invention relates to a kit of parts comprising a collecting device for collecting a tissue sample and a storage tube for storing the tissue sample therein. The collecting device comprises a punch and a plunger located within a bore of the punch and being adapted to slide within the bore. The storage tube comprises a tube body having an open first end, a closed second end, and a cap located at the first end of the tube body, the cap having a breakable seal that extends across the body of the tube to seal the first end of the tube body. The collecting device is adapted to break the seal of the cap and to fill the resulting opening to close off the storage tube.

8 Claims, 31 Drawing Sheets

(51) Int. Cl.
*A61D 1/00* (2006.01)
*G01N 1/04* (2006.01)
*A61B 10/00* (2006.01)
*B01L 3/00* (2006.01)

(52) U.S. Cl.
CPC ............ *A61B 10/0096* (2013.01); *A61D 1/00* (2013.01); *B01L 3/5082* (2013.01); *G01N 1/04* (2013.01); *A61B 2010/0208* (2013.01); *A61B 2503/40* (2013.01); *A61B 2562/08* (2013.01); *B01L 2200/0689* (2013.01); *B01L 2300/022* (2013.01); *B01L 2300/042* (2013.01); *B01L 2300/044* (2013.01); *B01L 2300/06* (2013.01); *B01L 2300/0672* (2013.01); *B01L 2300/12* (2013.01)

(56) References Cited

U.S. PATENT DOCUMENTS

| | | |
|---|---|---|
| 6,083,177 A | 7/2000 | Kobren et al. |
| 6,375,028 B1 | 4/2002 | Smith |
| 6,631,650 B1 * | 10/2003 | Espinosa .................. G01N 1/08 73/864.44 |
| 6,659,338 B1 | 12/2003 | Dittmann |
| 6,696,923 B2 | 2/2004 | Ishii et al. |
| 6,753,759 B2 | 6/2004 | Stegmaier et al. |
| 6,947,866 B2 | 9/2005 | Staab |
| 6,968,639 B2 | 11/2005 | Destoumieux |
| 7,235,055 B2 | 6/2007 | Pfistershammer |
| 7,467,760 B2 | 12/2008 | Schieli et al. |
| 7,528,725 B2 | 5/2009 | Stewart |
| 7,764,177 B2 | 7/2010 | Stewart |
| 7,764,181 B2 | 7/2010 | Stewart et al. |
| 7,791,409 B2 | 9/2010 | Arrigo |
| 7,936,272 B2 | 5/2011 | Stewart |
| 8,070,757 B2 | 12/2011 | Eadie |
| 8,159,291 B2 | 4/2012 | Arrigo |
| 8,361,416 B2 | 1/2013 | Berner |
| 8,581,705 B2 | 11/2013 | Stewart |
| 8,668,655 B2 | 3/2014 | Destoumieux |
| 8,763,287 B2 | 7/2014 | Hilpert |
| 8,854,188 B2 | 10/2014 | Stewart |
| 2002/0120216 A1 | 8/2002 | Fritz et al. |
| 2004/0103567 A1 | 6/2004 | Destoumieux |
| 2004/0167429 A1 | 8/2004 | Roshdieh |
| 2004/0167430 A1 | 8/2004 | Roshdieh |
| 2004/0232323 A1 | 11/2004 | Bosco et al. |
| 2005/0038355 A1 | 2/2005 | Gellman et al. |
| 2005/0228310 A1 | 10/2005 | Pfistershammer |
| 2005/0272057 A1 | 12/2005 | Abrahamsen |
| 2007/0239067 A1 | 10/2007 | Hibner |
| 2008/0064983 A1 | 3/2008 | Stromberg |
| 2008/0170967 A1 * | 7/2008 | Itoh ........................... B67B 7/02 422/400 |
| 2008/0227662 A1 | 9/2008 | Stromberg |
| 2008/0228105 A1 | 9/2008 | Howell et al. |
| 2009/0270878 A1 | 8/2009 | Eadie |
| 2010/0016758 A1 | 1/2010 | Hilbert |
| 2010/0066475 A1 | 3/2010 | Goldblatt |
| 2010/0160830 A1 * | 6/2010 | Schmiedl ........... A61B 10/0045 600/572 |
| 2010/0168616 A1 | 7/2010 | Schraga et al. |
| 2010/0210011 A1 | 8/2010 | Hilbert |
| 2010/0286556 A1 | 11/2010 | Decaluwe et al. |
| 2010/0291662 A1 | 11/2010 | Berner |
| 2011/0127177 A1 | 6/2011 | Hostettler |
| 2011/0269228 A1 | 11/2011 | Decaluwe |
| 2011/0295148 A1 | 12/2011 | Destoumieux |
| 2012/0010526 A1 * | 1/2012 | Hilpert .................. A01K 11/003 600/564 |
| 2012/0016263 A1 * | 1/2012 | Hilpert .................. A01K 11/003 600/567 |
| 2013/0040358 A1 | 2/2013 | Woods |
| 2013/0204159 A1 | 8/2013 | Destoumieux |
| 2013/0211287 A1 | 8/2013 | Decaluwe |
| 2013/0211416 A1 | 8/2013 | Teychene |
| 2014/0249449 A1 | 9/2014 | Hilpert |
| 2015/0112225 A1 | 4/2015 | Prow et al. |
| 2015/0226646 A1 | 8/2015 | Lardi et al. |
| 2016/0007567 A1 | 1/2016 | Decaluwe et al. |

FOREIGN PATENT DOCUMENTS

| | | |
|---|---|---|
| CN | 2466626 Y | 12/2001 |
| CN | 1921803 A | 2/2007 |
| CN | 101352357 A | 1/2009 |
| CN | 101438969 A | 5/2009 |
| CN | 202044292 U | 11/2011 |
| CN | 102271592 A | 12/2011 |
| CN | 101352356 B | 11/2012 |
| CN | 101438969 B | 11/2012 |
| CN | 102933157 | 2/2013 |
| CN | 103052313 | 4/2013 |
| CN | 102271592 B | 11/2014 |
| DE | 19835014 | 8/1999 |
| DE | 20022647 | 1/2002 |
| DE | 202004015643 U1 | 1/2005 |
| EP | 0016236 | 10/1980 |
| EP | 982688 | 3/2000 |
| EP | 1014861 | 7/2000 |
| EP | 1060662 | 12/2000 |
| EP | 1318718 | 6/2003 |
| EP | 1781086 | 9/2007 |
| EP | 1920651 | 5/2008 |
| EP | 1809096 | 2/2009 |
| EP | 2066170 | 6/2009 |
| EP | 2068718 | 6/2009 |
| EP | 2160093 | 3/2010 |
| EP | 2168207 | 3/2010 |
| EP | 2249966 | 11/2010 |
| EP | 2265109 | 12/2010 |
| EP | 2307136 | 4/2011 |
| EP | 2355653 | 8/2011 |
| EP | 2378863 | 10/2011 |
| EP | 2384618 | 11/2011 |
| EP | 2384619 | 11/2011 |
| EP | 1718142 | 10/2012 |
| EP | 2579781 | 4/2013 |
| EP | 2579782 | 4/2013 |
| EP | 2597944 | 6/2013 |
| EP | 2736324 | 6/2014 |
| EP | 2770819 | 9/2014 |
| FR | 2939281 | 6/2010 |
| GB | 2358061 | 7/2001 |
| GB | 2482036 | 1/2012 |
| IN | 201200015 | 5/2012 |
| JP | 10225459 | 8/1998 |
| JP | 2006026227 | 2/2007 |
| JP | 2012511310 | 5/2012 |
| JP | 2012514201 | 6/2012 |
| JP | 2012526966 | 11/2012 |
| JP | 2013079859 | 5/2013 |
| NZ | 503521 | 12/2002 |
| NZ | 575341 | 1/2012 |
| NZ | 593039 | 12/2012 |
| NZ | 596853 | 2/2014 |
| NZ | 608927 | 11/2014 |
| SU | 946387 | 7/1982 |
| WO | 200051496 | 9/2000 |
| WO | 2002023980 | 3/2002 |
| WO | WO 2002039810 | 5/2002 |
| WO | WO 2005101273 | 10/2005 |
| WO | 2006000869 | 1/2006 |
| WO | 2007013280 | 2/2007 |
| WO | 2007013820 | 2/2007 |
| WO | 2008037802 | 4/2008 |
| WO | 2008040692 | 4/2008 |
| WO | 2008101497 | 8/2008 |
| WO | 2009010658 | 1/2009 |
| WO | WO 2009008861 | 1/2009 |
| WO | 2009046957 | 4/2009 |
| WO | 2009095178 | 8/2009 |
| WO | 2009127541 | 10/2009 |

(56) References Cited

FOREIGN PATENT DOCUMENTS

| WO | WO 2009120206 | 10/2009 | | |
|---|---|---|---|---|
| WO | 2010012446 | 2/2010 | | |
| WO | 2010066475 | 6/2010 | | |
| WO | 2010070129 | 6/2010 | | |
| WO | 2010070130 | 6/2010 | | |
| WO | WO 2010066475 | 6/2010 | | |
| WO | WO-2010066475 A1 * | 6/2010 | ........... | A01K 11/003 |
| WO | WO 2010070130 | 6/2010 | | |
| WO | WO 2011044585 | 4/2011 | | |
| WO | 2011073359 | 6/2011 | | |
| WO | 2011154233 | 12/2011 | | |
| WO | 2011154510 | 12/2011 | | |
| WO | 2011154510 A1 | 12/2011 | | |
| WO | 2012013429 | 2/2012 | | |
| WO | 2013060690 | 5/2013 | | |
| WO | WO 2013155557 | 10/2013 | | |
| WO | 2014153181 | 9/2014 | | |
| WO | WO 2015014461 | 2/2015 | | |
| WO | WO 2015158787 | 10/2015 | | |
| WO | WO 2016016204 | 2/2016 | | |
| WO | WO 2016073754 | 5/2016 | | |

OTHER PUBLICATIONS

International Preliminary Report on Patentability for Application No. PCT/IB2014/065395 dated Sep. 2, 2015 (4 pages).
International Search Report and Written Opinion from the International Searching Authority for Application No. PCT/IB2014/065397 dated Feb. 26, 2015 (9 pages).
International Preliminary Report on Patentability for Application No. PCT/IB2014/065397 dated Feb. 3, 2015 (3 pages).
International Search Report and Written Opinion from the International Searching Authority for Application No. PCT/IB2014/065393 dated Feb. 3, 2015 (15 pages).
International Preliminary Report on Patentability for Application No. PCT/IB2014/065393 dated Feb. 3, 2016 (6 pages).
International Search Report and Written Opinion from the International Searching Authority for Application No. PCT/IB2014/065396 dated Feb. 19, 2015 (13 pages).
Office Action from the U.S. Patent and Trademark Office for U.S. Appl. No. 14/896,325 dated Sep. 27, 2018 (18 pages).
Office Action from the U.S. Patent and Trademark Office for U.S. Appl. No. 15/030,211 dated Nov. 20, 2018 (12 pages).
Office Action from the U.S. Patent and Trademark Office for U.S. Appl. No. 15/030,203 dated Feb. 1, 2019 (12 pages).

* cited by examiner

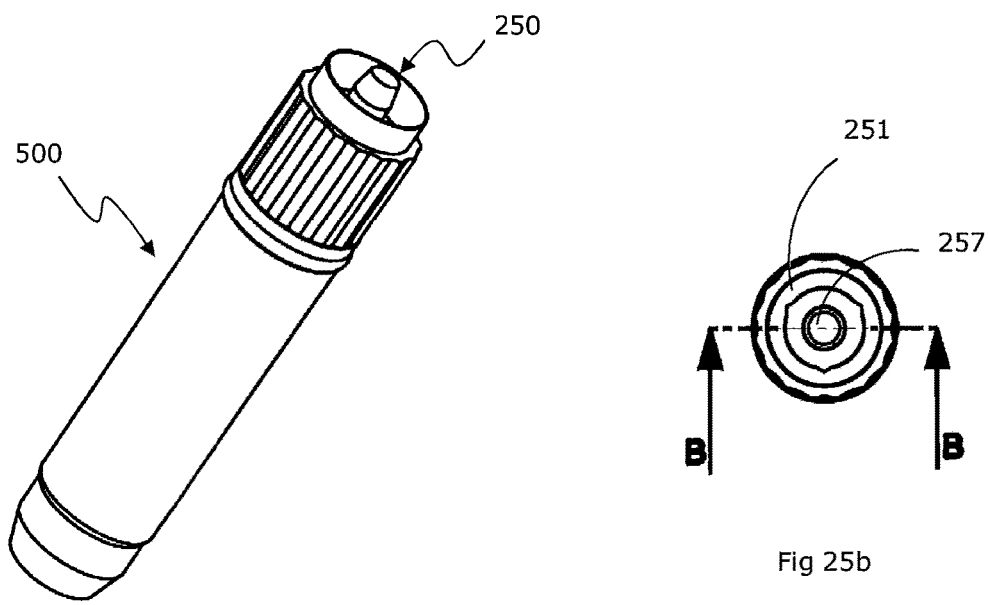
Fig 25a
Fig 25b
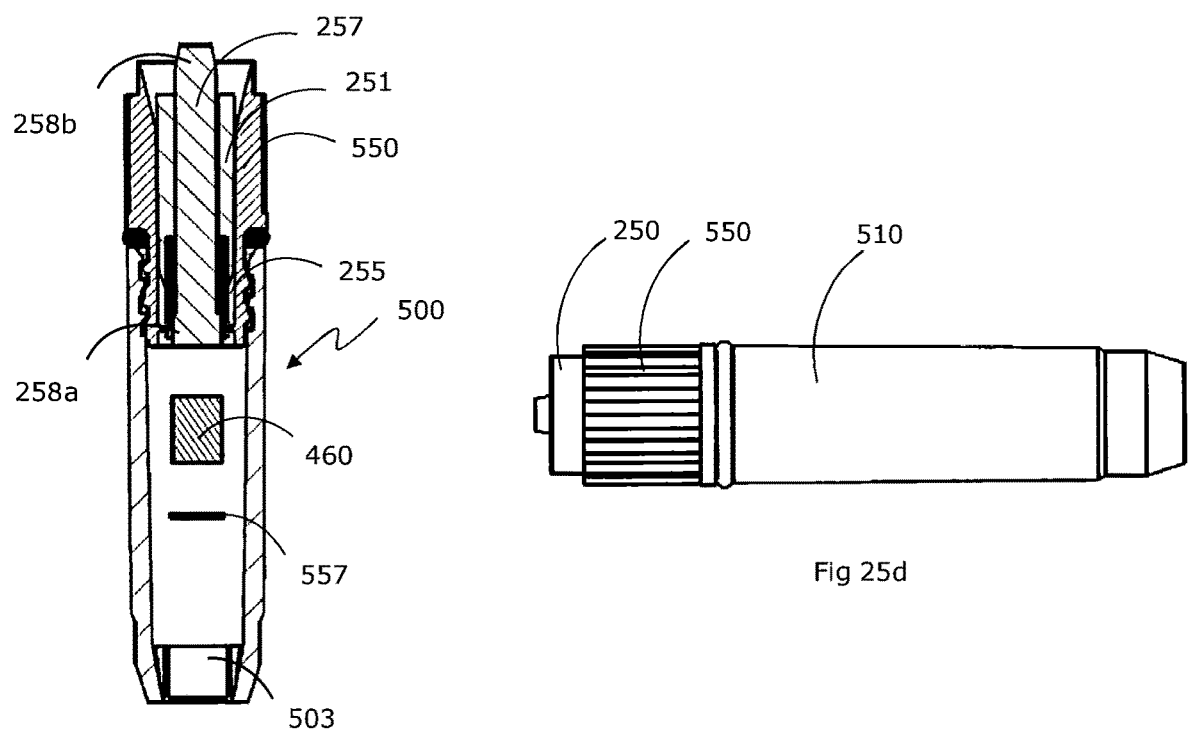
Fig 25c
Fig 25d

TISSUE SAMPLING

CROSS-REFERENCE TO RELATED APPLICATIONS

This application is a national stage filing under 35 U.S.C. § 371 of International Application No. PCT/NZ2014/000107, filed Jun. 5, 2014, which claims priority to New Zealand Application No. 611547, filed Jun. 5, 2013, and New Zealand Application No. 616807, filed Oct. 18, 2013. The entire contents of all three applications are incorporated herein by reference.

FIELD OF THE INVENTION

The invention relates to improvements in and relating to tissue sampling and in particular the obtaining of tissue samples from animals or plants.

BACKGROUND OF THE INVENTION

To improve the tracking of livestock and to facilitate DNA testing, tissue samples may be collected from animals. A tissue sample may be taken from an animal at any time and is often taken at the same time as placing an identification tag on the animal. The tissue sample is usually cut from an animal using a tissue sampling device and is placed in a storage container for laboratory analysis.

New Zealand patent numbers 593039 and 604083 describe a tissue sampler in the shape of a clamp and comprising a pair of jaws that move toward each other to take a tissue sample. A cutting element is located in one of the jaws and is forced through an animal's ear, for example, to cut a plug of tissue from the ear as the jaws are clamped together using a first actuation action. A plunger is used to push the tissue sample out of the cutting element and into a storage tube held by the other jaw of the tissue sampler. The storage tube has a closed end and an opposing capped end. The capped end of the tube comprises an aperture through which the tissue sample is pushed by the plunger. The plunger remains in the aperture of the storage tube cap to seal the tube before the tube is removed from the device and taken away for analysis.

After the storage tube is removed, the cutting element needs to be removed from the sampler because the a different cutting element needs to be used for each tissue sample to prevent contamination of the tissue sample. The cutting element can be automatically ejected through a second actuation action of the sampler. The cutting element is then discarded onto the ground or into a refuse container. The cutting elements are sharp, so handling the cutting element carries a risk of being cut. Discarding the cutting element on the ground also carries this risk.

After the cutting element has been removed, a new cutting element, plunger, and storage tube need to be added to the tissue sampler before another tissue sample can be collected. Therefore, when the tissue sampling device is to be used, it is necessary for the user to load a new punch into the sampling device, cut a tissue sample, and to then remove the used punch before loading the next new punch into the device. The loading and unloading of punches is done manually and is a slow and fiddly process.

When the storage tube is removed for analysis, it is necessary for the cap of the storage tube (containing the plunger) to be removed before the tissue sample can be extracted. Because of the design of the tube and cap, each cap needs to be removed individually in the laboratory, which is a time consuming and therefore costly process.

It is an object of the present invention to provide: (a) a tissue sampler that goes at least some way toward overcoming the disadvantages of known tissue samplers (b) a collecting means that goes at least some way toward overcoming the disadvantages of known collecting means; or (c) a useful alternative to known tissue sampling devices and methods.

SUMMARY OF THE INVENTION

In one aspect, the invention provides a kit of parts comprising a collecting device for collecting a tissue sample and a storage tube for storing the tissue sample therein, the collecting device comprising a punch having a cutting element with a cutting edge formed at a cutting end of the punch and also comprising a centrally located bore that extends through the punch and cutting element, wherein the cutting element surrounds one end of the bore at the cutting end of the punch to form a surrounding wall within which a sample holding cavity is held, wherein the collecting device also comprises a plunger having a first end and an opposing second end, the plunger being located within the bore of the punch and being adapted to slide within the bore and the sample holding cavity and toward the cutting edge of the punch, wherein the storage tube comprises a tube body having an open first end, a closed second end, and wherein the storage tube also comprises a cap at the first end of the tube body, the cap having a breakable seal that extends across the body of the tube to seal the first end of the tube body.

Preferably, the cutting edge is adapted to break the seal of the storage tube cap to form an opening to the tube body and wherein the collecting device is adapted to be held within the opening in the cap of the storage tube to close off the first end of the tube. Preferably, the seal is in the form of a membrane.

Preferably, the first end of the plunger is enlarged. Optionally, the first end of the plunger comprises a non-stick material on its surface. Preferably, the plunger comprises an RFID device.

Preferably, the second end of the plunger projects from the pushing end of the punch when the collecting device is held within the cap of the storage tube. More preferably, the collecting device is adapted so that the second end of the plunger can be depressed toward the pushing end of the punch to cause the first end of the plunger to push a tissue sample out of the sample holding cavity.

In another aspect, the invention provides a method of decapping a storage tube comprising a tube body having an open first end, a closed second end, and a removable cap attached to the first end of the tube body, wherein a collecting device is located within an opening formed in the cap and acts to close off the first end of the storage tube body, the collecting device comprising a punch having a cutting element with a cutting edge formed at a cutting end of the punch and also comprising a centrally located bore that extends through the punch and cutting element, wherein the cutting element surrounds one end of the bore at the cutting end of the punch to form a surrounding wall within which a sample holding cavity is held, wherein the collecting device also comprises a plunger having a first end and an opposing second end, the plunger being located within the bore of the punch and being adapted to slide within the bore and the sample holding cavity and toward the cutting edge of the punch, wherein the second end of the plunger projects from the pushing end of the punch and the first end of the plunger is located within the bore of the punch, the method comprising the steps of: depressing the second end of the plunger toward the pushing end of the punch to cause the first end of the plunger to push a tissue sample out of the sampler holding cavity and into the storage tube body; and removing the cap, including the collecting device held therein, from the storage tube body to access the tissue sample within the tube body.

Preferably, the storage tube is one of a plurality of storage tubes, each storage tube being held within a cell of a multi-cell rack. More preferably, each of the storage tubes are decapped simultaneously by a machine.

According to another aspect, the present invention provides a tissue sampling apparatus including a punch and a tissue sample storage tube, the tube having an opening at an upper end which is adapted to be closed off by a lower end, the tube having an opening at an upper end which is adapted to be closed off by a lower end of the punch after it has passed through a part of an animal and captured a tissue sample, the end of the punch being further adapted to retain the tissue sample temporarily until it can be automatically released into the sample tube. Preferably, the upper end of the sample tube may include a seal which is broken by the passage therethrough of the end of the punch. Preferably the seal is in the form of a membrane.

Preferably an opposite end of the sample tube includes engagement means adapted to engage with a base of a sample tube holder in preventing rotation within and/or withdrawal from, the sample holder.

According to another aspect of the present invention there is provided a tube holder having a plurality of cells, each adapted to receive therein a storage tube, a base of each cell being adapted to engage with a closed end of a respective storage tube, an upper end of each storage tube including a cap holding a collecting device therein, which collected the sample, the cap being removable when access to the sample within the tube is required.

As used in this specification, the words "comprises", "comprising", and similar words, are not to be interpreted in an exclusive or exhaustive sense. In other words, they are intended to mean "including, but not limited to".

Any reference to prior art documents in this specification is not to be considered an admission that such prior art is widely known or forms part of the common general knowledge in the field.

BRIEF DESCRIPTION OF THE DRAWINGS

Preferred forms of the invention will now be described by way of example only and with reference to the accompanying drawings, in which:

FIG. 1b is a front view of the tissue sampler of FIG. 1a;

FIG. 1c is a cross-sectional side view of the tissue sampler taken along line A-A of FIG. 1a;

FIG. 8b is a side view of the punch of FIG. 8a;

FIG. 8c is an end view showing the pushing end of the punch of FIG. 8a;

FIG. 8e is an end view showing the cutting end of the punch of FIG. 8a;

FIG. 9b is a side view of the tube body of FIG. 9a;

FIG. 9c is a cross-sectional side view of the tube body taken along line A-A of FIG. 9a;

FIG. 9d is an end view of the closed second end of the tube body of FIG. 9a;

FIG. 25a is a perspective view of a storage tube in which the plunger of a collecting device held in the cap of the tube has been depressed;

FIG. 25b is an end view of the first end of the storage tube of FIG. 25a in which the collection device is held;

FIG. 25c is a cross-sectional side view of the storage tube of FIG. 25a in which the tissue sample has been released from the collecting device;

FIG. 25d is a side view of the storage tube of FIG. 25a;

FIG. 28b is a cross-sectional side view of the storage tubes taken along line A-A of FIG. 28a.

DETAILED DESCRIPTION OF PREFERRED FORMS OF THE INVENTION

The present invention relates to a tissue sampler for obtaining tissue samples from plants and animals particularly, including pigs, goats, cattle, sheep, poultry, and fish. The tissue sampler may be used with or without simultaneous placing of an identification tag. The invention also relates to collecting device and to a storage tube cap for use when collecting a tissue sample for later analysis. In addition, the invention relates to a method of taking a tissue sample and to a method of ejecting a tissue sample from a collecting device.

The tissue sampler of the invention is adapted to hold a rotatable magazine comprising a plurality of collecting devices. Each collecting device comprises a punch having a cutting element for cutting a sample from tissue (such as animal tissue or plant material for example). Each collecting device also comprises a plunger that pushes the sample into a storage tube held by the tissue sampler by movement of an actuating means. After a tissue sample is taken, the magazine can be rotated to bring another collecting device into position for taking another sample, so that sequential tissue samples can be taken efficiently.

Figure 1A:
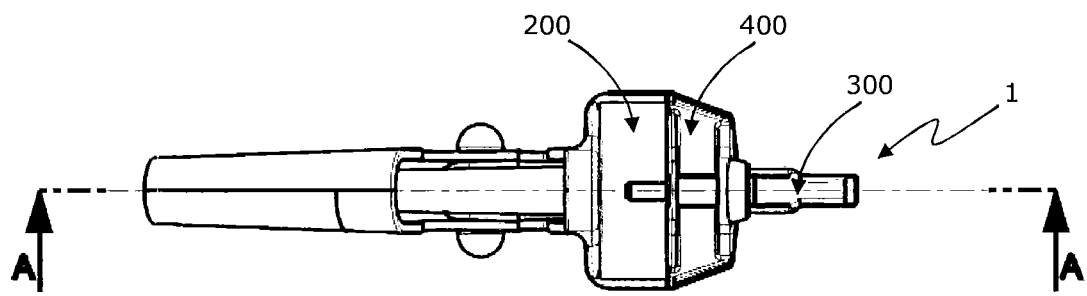
FIG. 1a is a top view of one form of tissue sampler according to the invention.
Figure 1B:
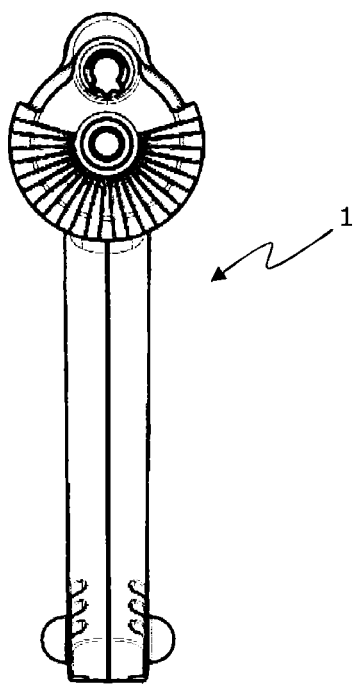
Figure 1C:
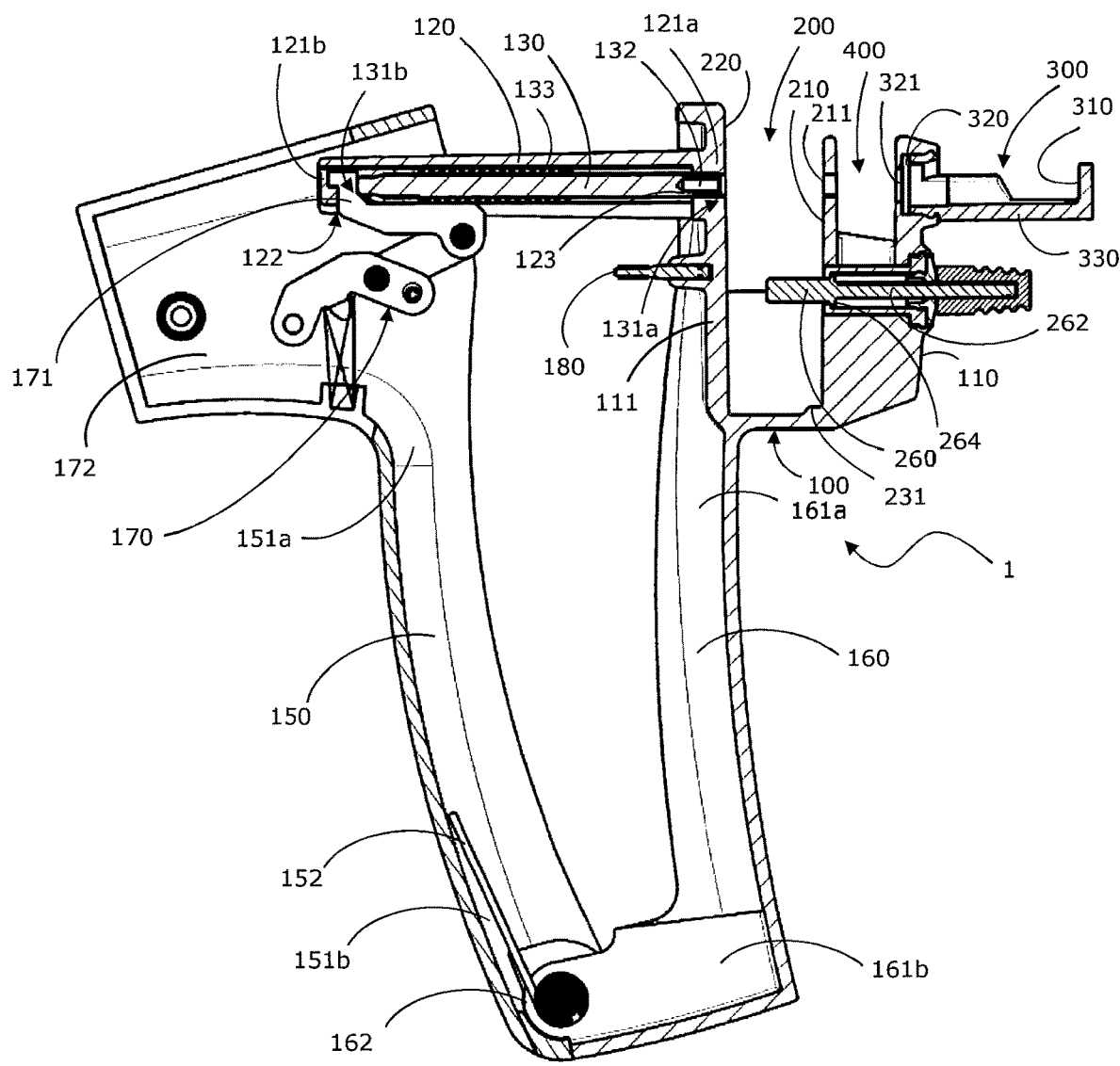

In one form, as shown in FIGS. 1a to 1c, the tissue sampler 1 comprises a body 100 having a magazine housing 200, a storage tube holder 300, and a cutting region 400. The cutting region is located between the magazine housing and storage tube holder.

Figure 2:
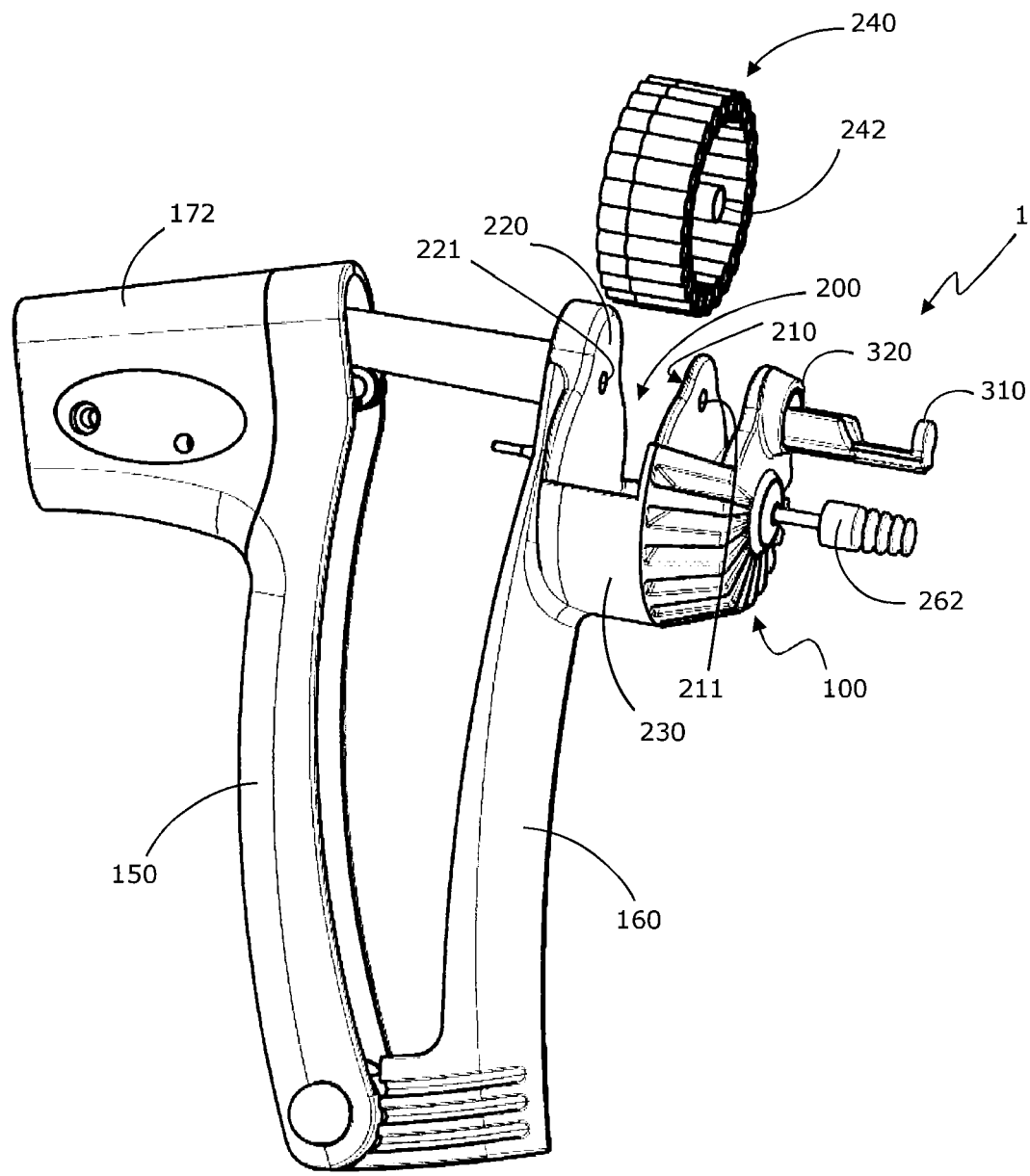
FIG. 2 is a perspective view of the tissue sampler of FIG. 1a with a collecting device magazine about to be placed into the magazine housing of the tissue sampler.
Figure 3:
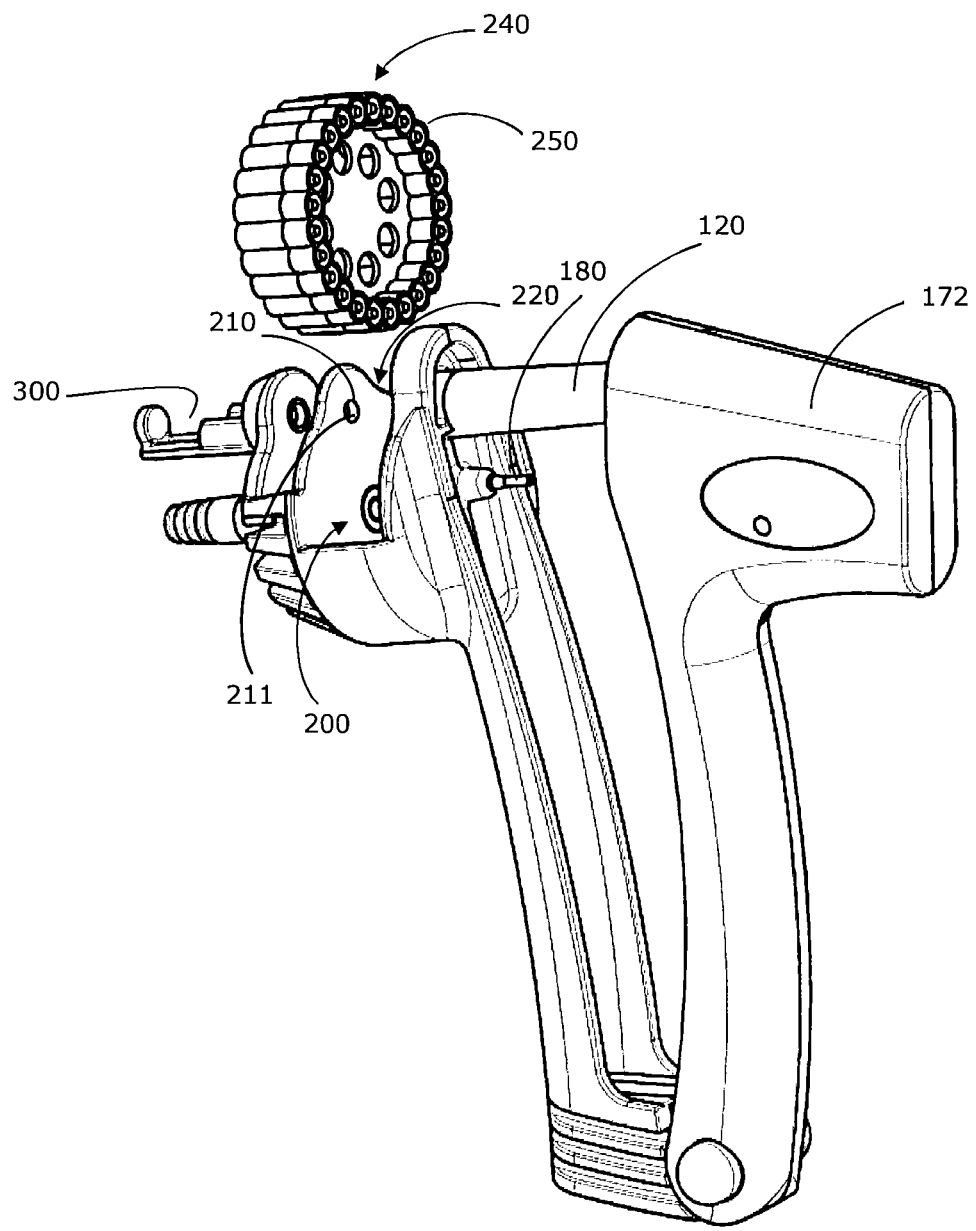
FIG. 3 is another perspective view of the tissue sampler shown in FIG. 2.

As shown in FIGS. 2 and 3, the magazine housing 200 is adapted to hold a collecting device magazine 240, for holding a plurality of collecting devices 250 therein. The magazine housing 200 comprises a front wall 210, a rear wall 220, and at least one connecting wall 230 that extends between the front and rear walls. In one form, the connecting wall 230 is a curved wall located at the bottom of the magazine housing to form a cradle for a substantially cylindrical collecting device magazine to be held within the magazine housing. In this form, at least a portion of the sides and top of the holder are open to allow a collecting device magazine to be loaded into the magazine housing and accessed from above or from the side. However, the magazine housing may be of any suitable configuration to hold a collecting device magazine therein. For example, the magazine housing may be substantially enclosed and comprise a door through which a magazine can be loaded into the holder.

The front wall 210 of the magazine housing comprises a cutting region aperture 211 connecting to the cutting region and through which a collecting device can be pushed to access the cutting region located on the other side of the front wall 210 of the magazine housing. The rear wall 220 of the holder comprises a ram receiving aperture 221 that aligns with the cutting region aperture 211 of the front wall. The magazine housing is adapted so that when a collecting device magazine 240 is placed within the holder 200, a collecting device can be positioned between the apertures 211 and 221.

Figure 4:
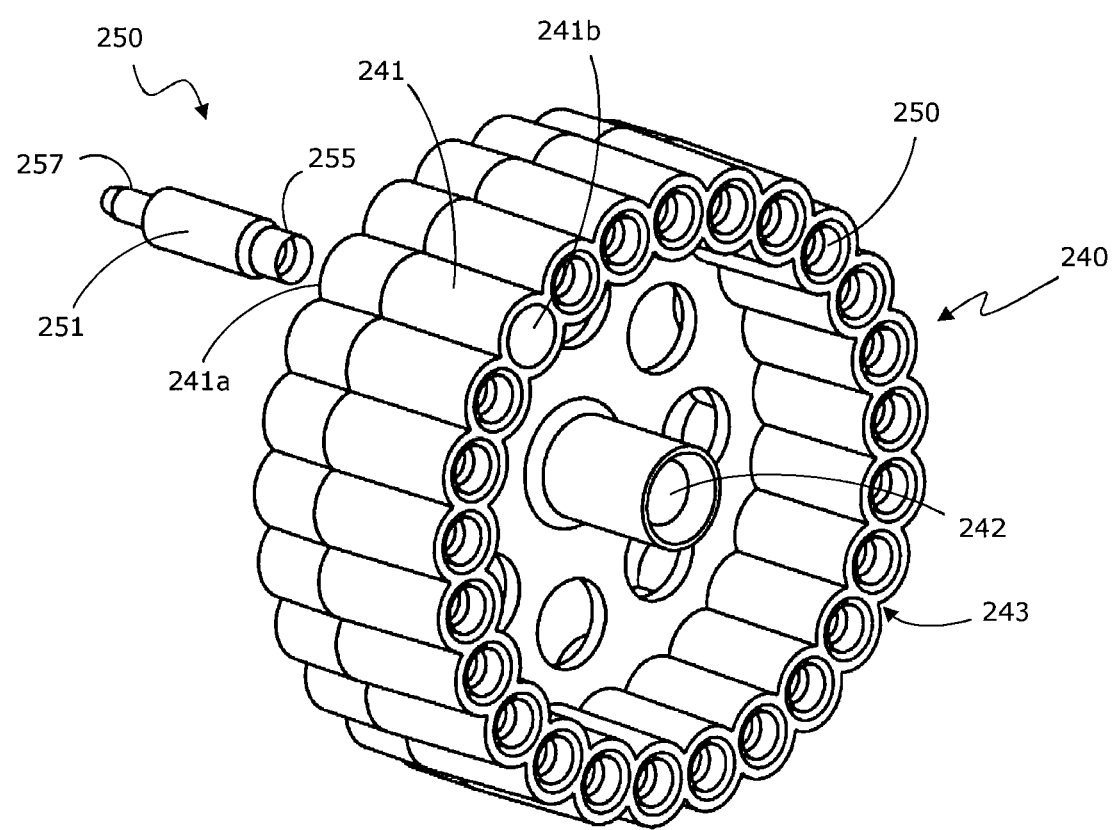
FIG. 4 is a perspective view of a collecting device magazine according to one aspect of the invention.

As shown in FIGS. 2 to 4, the magazine housing 200 is sized to receive a magazine 240 comprising a plurality of chambers 241, each chamber being adapted to hold a collecting device 250 therein and having open first and second opposing ends 241a, 241b. The magazine, (see particularly FIG. 4), is preferably in the form of a cylinder having a centrally located bore 242 that extends along the length of the magazine. The chambers are positioned concentrically around the bore and preferably near the circumference of the magazine. Preferably, at least a portion of the chambers in the magazine 240 is of a transparent material, so that the presence of a collecting device in any of the chambers can be identified. In the embodiment shown in FIG. 4, the magazine comprises 25 chambers, although the magazine may have any suitable number of chambers, provided that the magazine is sized to fit within the magazine housing and is adapted to position a plurality of collecting devices (one after the other) between the apertures 211 and 221, as described below.

Figure 5:
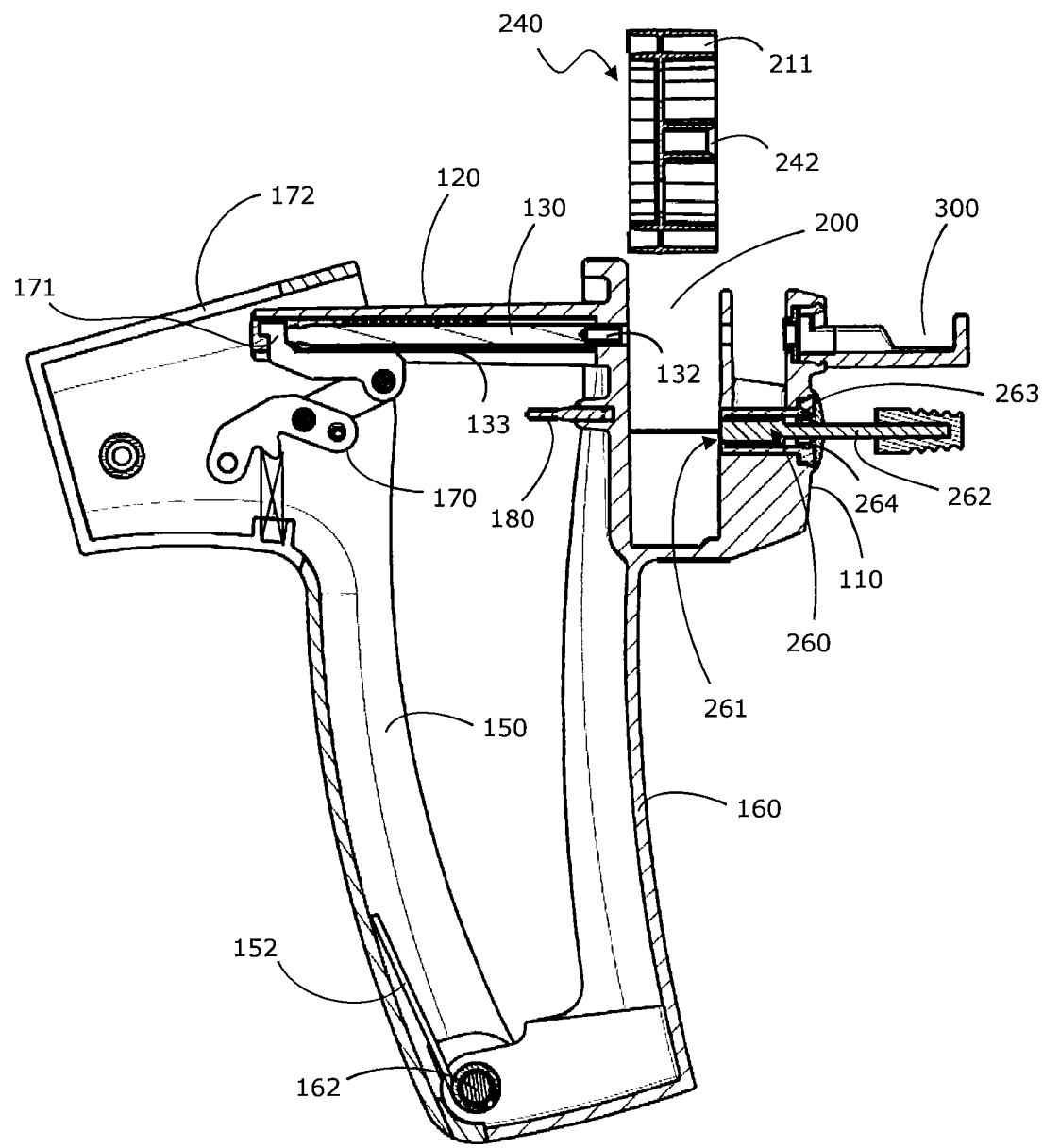
FIG. 5 is a cross-sectional side view of one form of tissue sampler according to the invention in which the magazine locator is retracted.

In one form, as shown in FIGS. 1c and 5, the tissue sampler comprises a magazine in the form of a spindle 260 or the like that is partially located within a locator housing 265 and is able to project into the magazine housing through a locator receiving aperture 261, located in the front wall 210 of the magazine housing, that connects the locator housing to the magazine housing.

The spindle is connected with a locator release pin 262, which is adapted to retract the spindle from the magazine housing so that a magazine can be loaded and unloaded into the holder 200. A free end of the release pin projects from a front wall 110 of the body of the tissue sampler and is optionally surrounded in a material, such as plastic or rubber for example, that makes it easier for a user to grip the release pin, as shown in FIG. 1c.

The locator release pin is adapted to be pulled away from the body to a retracted position, as shown in FIG. 5, in which the spindle is retracted from the magazine housing so that a used magazine can be removed from the magazine housing and replaced with a new magazine. Similarly, when the release pin is returned to its rest position, the spindle is caused to project through the locator receiving aperture and into the magazine housing in a locating position. In the locating position, the spindle 260 is able to project into with the bore 242 of a magazine held in the magazine housing 200 to hold the magazine in position within the holder 200. Preferably, the spindle is biased to the locating position using a locator biasing means. Any suitable form of biasing means may be used.

In the embodiment shown in FIGS. 1a and 5, the spindle 260 is biased to the locating position with a locator biasing means in the form of a compression spring 263. In this form, the locator release pin 262 is substantially cylindrical and extends from one end of the spindle. The release pin has a smaller diameter than the spindle. Optionally, a collar 264 projects from the periphery of the spindle at the location where the spindle connects to the release pin. The compression spring 263 surrounds the portion of the release pin that is located between a front wall 110 of the tissue sampler body and the collar 264. In the embodiment where the spindle does not include a collar, the compression spring is located between the front wall of the body and the shoulder provided by the end of the spindle that meets with the smaller diameter release pin. Therefore, one end of the compression spring abuts the front wall of the body and the other end abuts the spindle (either the collar or shoulder of the spindle, as the case may be). In this arrangement, as the locator release pin 262 is pulled to retract the spindle from the magazine housing, the collar/shoulder 264 of the spindle moves toward the front wall 110 of the tissue sampler body so that the compression spring 263 is compressed. As soon as the release pin 262 is released, the compression spring 263 extends to its natural rest position, pushing the release pin 262 back toward the front wall 110 of the tissue sampler body to its rest position and simultaneously pushing the spindle 260 through the locator receiving aperture 261 and into the magazine housing 200 to the locating position.

Figure 6:
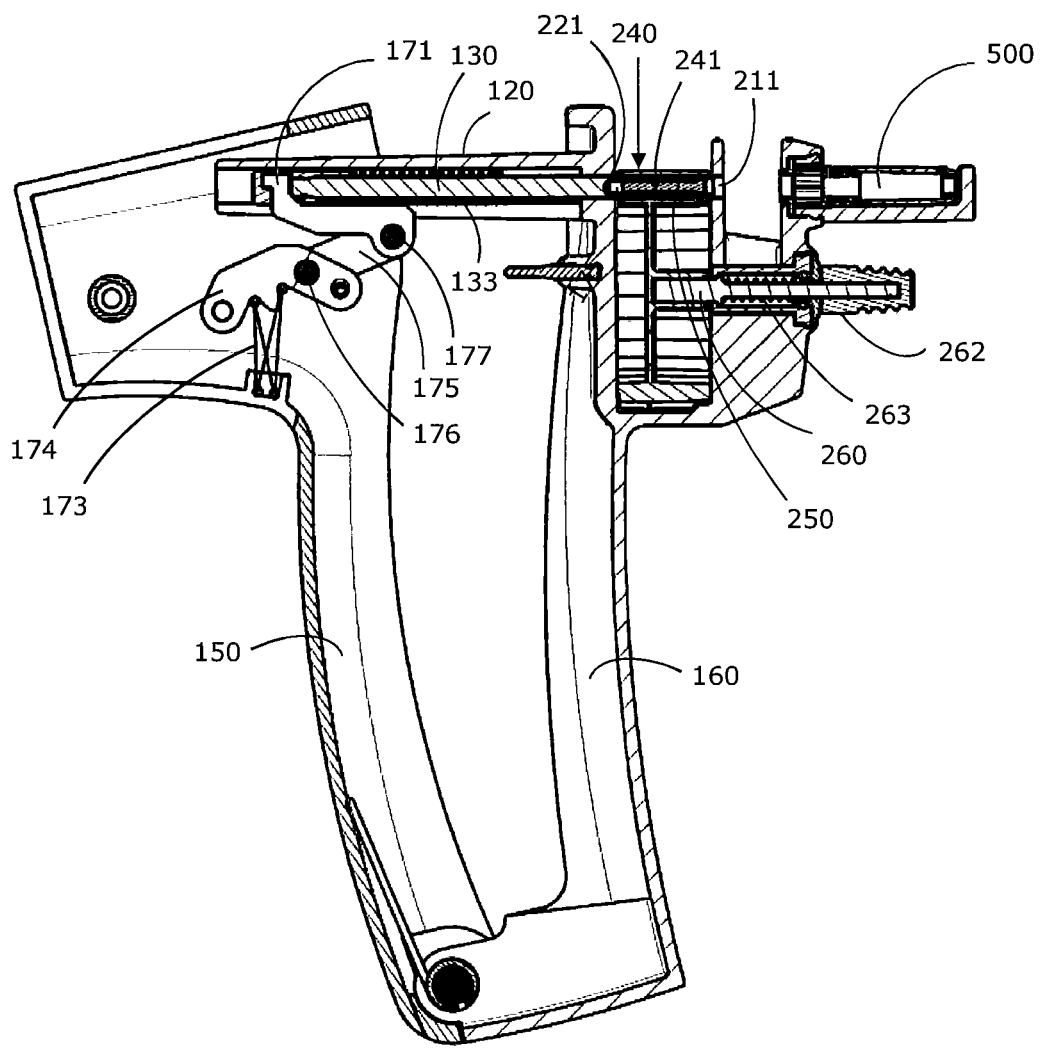
FIG. 6 is a cross-sectional side view of the tissue sampler of FIG. 1a in which a collecting device in a chamber of a magazine housing is in the active position.
Figure 7A:
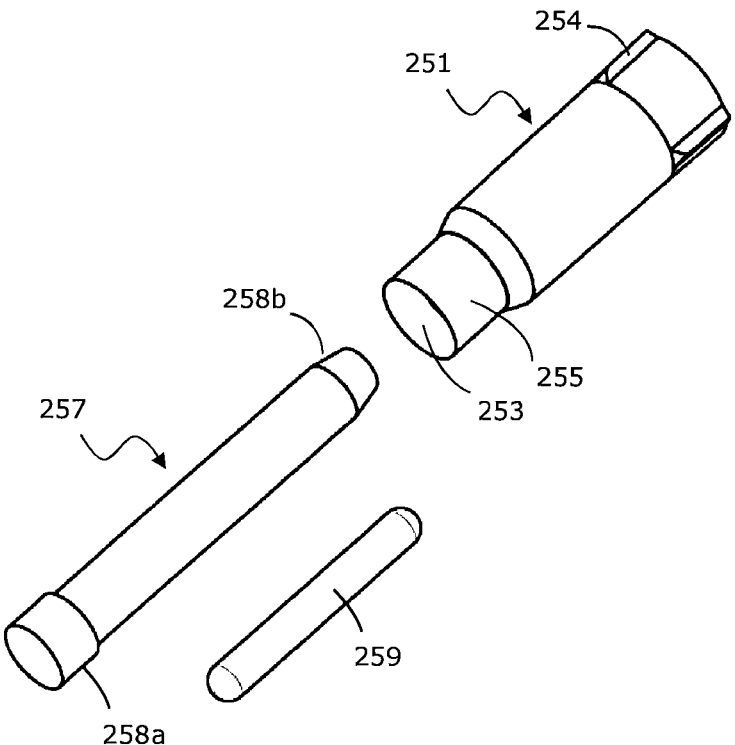
FIG. 7a is an exploded view of one form collecting device according to the invention.
Figure 7B:
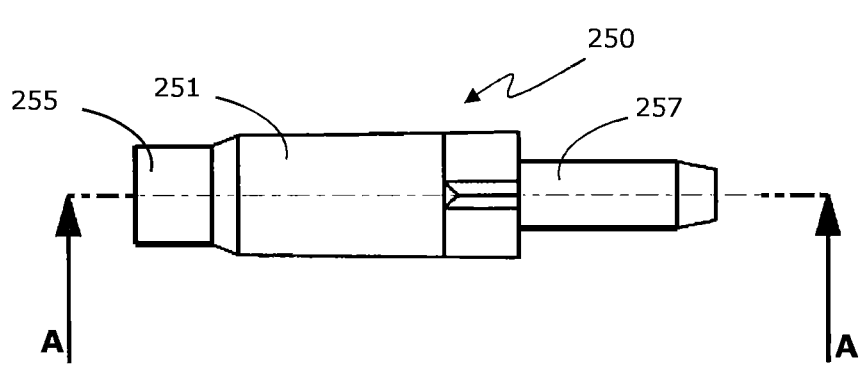
FIG. 7b is a side view of one form of collecting device.
Figure 7C:
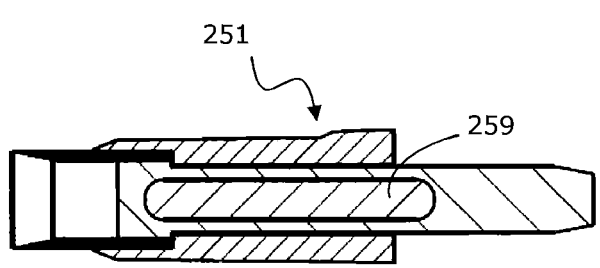
FIG. 7c is a cross-sectional side view of the collecting device taken along line A-A of FIG. 7b.
Figure 7D:
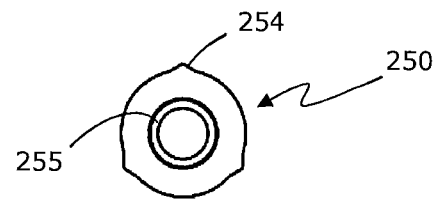
FIG. 7d is an end view of the collecting device of FIG. 7b.
Figure 7E:
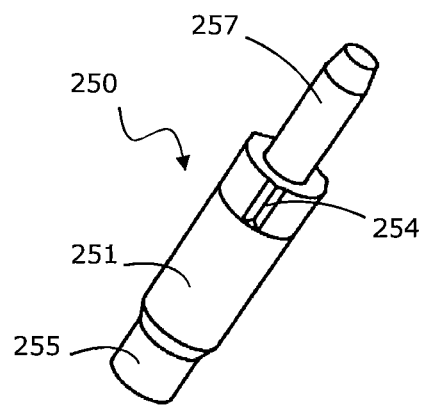
FIG. 7e is a perspective view of another form of collecting device according to the invention.
Figure 7F:
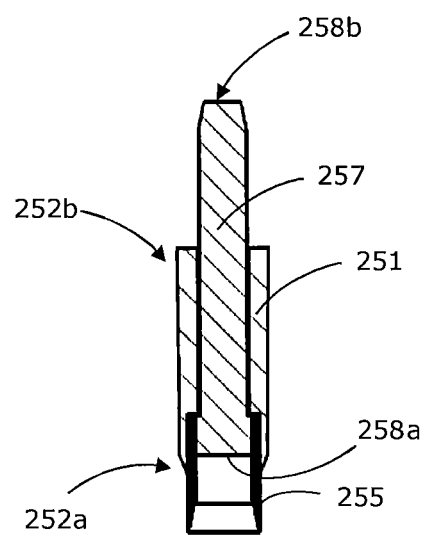
FIG. 7f is a cross-sectional side view of the collecting device of FIG. 7e.
Figure 8A:
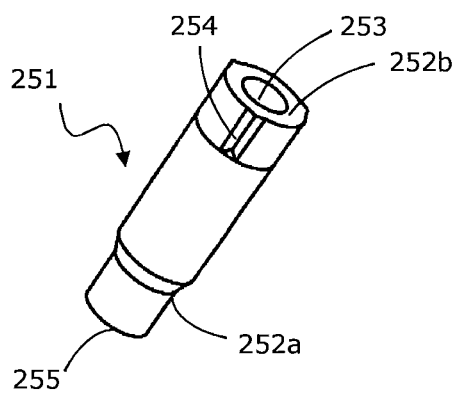
FIG. 8a is a perspective view of one form of punch for a collecting device according to the invention.
Figure 8B:
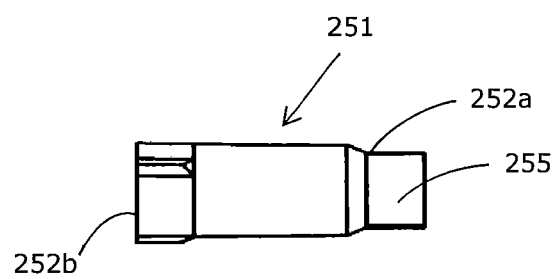
Figure 8C:
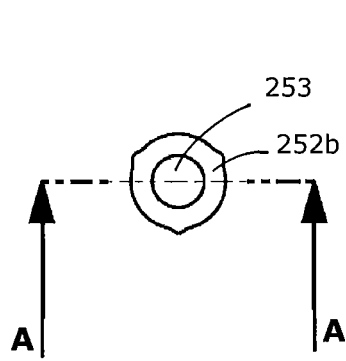
Figure 8D:
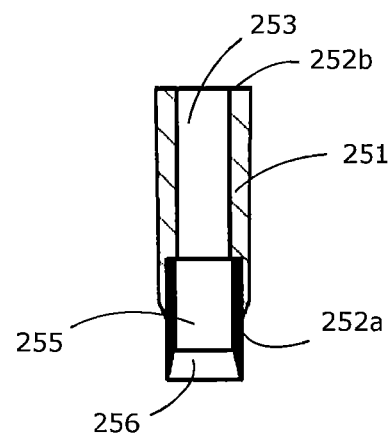
FIG. 8d is a side view of the punch taken along line A-A of FIG. 8c.
Figure 8E:
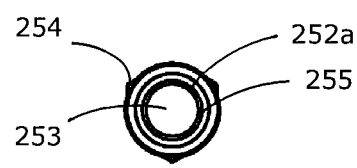

As shown in FIG. 6, a magazine is positioned within the magazine housing so that one of the chambers 241 aligns with both the ram receiving aperture 221 and the cutting region aperture 211. A collecting device 250 within the aligned chamber 241 will therefore also align with the apertures 211, 221. When aligned with these apertures 211, 221, the collecting device 250 is in the collecting position and will be referred to in this specification as the active collecting device. A chamber having a collecting device in the collecting position will be referred to in this specification as the active chamber.

The magazine is able to rotate within the magazine housing so that unused collecting devices can be sequentially moved into the collecting position. Typically, the magazine is adapted to rotate incrementally, so that sequential punches can be rotated into the collecting position one by one, as tissue samples are sequentially taken. The magazine may be adapted to be rotated manually or by some mechanical or electrical operator. The magazine may also involve a ratchet mechanism or the like so that the magazine can be rotated incrementally to its next position. To help locate the active chamber to be aligned with apertures 211 and 221, the magazine and magazine housing may comprise chamber locating means. For example, the magazine housing may comprise at least one projection and/or recess for engaging with at least one corresponding recess and/or projection formed in the magazine. In the embodiment shown in FIG. 1c, the chamber locating means comprises a projection 231 formed in the connecting wall of the magazine housing that engages with a recess 243 formed in the magazine, as shown in FIG. 4. The projection snap fits into the recess when a chamber is aligned with the apertures 211 and 221 to hold the magazine in position. To rotate the magazine to align the next chamber with apertures 211 and 221, a degree of force is used. The magazine is formed of a resilient, at least partially flexible material and is able to flex around the projection 231 as the magazine is rotated until the projection engages with the next recess 243 in the magazine.

In one form, the central bore 242 of the magazine 240 is substantially cylindrical and the spindle 260 projecting into the magazine housing 200 is also substantially cylindrical so that the magazine can be rotated about the spindle by manually turning the magazine within the magazine housing or by using a mechanical system to rotate the magazine about the spindle. In another form, the spindle and the central bore of the magazine are shaped to engage with each other so that rotation of the spindle causes the magazine to rotate and vice versa. For example, the spindle may have a star shaped cross-section and the bore of the magazine may have a correspondingly star shaped cross-section. In this form, it is possible to rotate the magazine by rotating the release pin of the spindle.

The collecting device to be used with the tissue sampler of the invention comprises a punch having a cutting element with a cutting edge 255a for cutting a plug of tissue. The cutting element extends from and surrounds one end of the bore of the punch at the cutting end of the punch to form a surrounding wall within which a sample holding cavity is held. The tissue sample cut by the punch is then held within the tissue holding cavity. The collecting device also comprises a plunger that extends through a bore of the punch to push the plug of sample tissue out of the tissue holding cavity and into a storage tube held by the tissue sampler. Any suitable commercially available collecting device may be used with the tissue sampler of the invention.

FIGS. 7a to 7e show preferred forms of collecting devices 250 according to another aspect of the invention. The collecting devices can be used with the tissue sampler 1 of the invention or with any other suitable tissue sampler. The collecting device of the invention comprises a punch 251 having a body with a cutting end 252a and an opposing pushing end 252b and a bore 253 that extends along the length of the punch between the cutting end and the pushing end, as shown in FIGS. 8a to 8e. Preferably, the punch has an elongate body and the bore is centrally located within the body of the punch. In one form, the outer surface of the body of the punch comprises guiding means in the form of one or more projections or recesses to locate the punch within a cap of a storage tube, as will be described later. In the embodiment shown in FIGS. 8a to 8d, the guiding means comprise three evenly spaced ribs 254 that project from the pushing end 252b of the punch.

A cutting element 255 is provided at the cutting end 252a of the punch to cut a sample of tissue from a sample specimen, such as an animal or plant. The cutting element may be attached to the punch or it may be integral with the punch so that the cutting element and punch are formed as a single part. The cutting element 255 extends from and surrounds one end of the bore 253 of the punch at the cutting end of the punch body to form a projecting surrounding wall or walls. In this way, the cutting element provides a bore that substantially aligns with the bore formed in the body of the punch. For the sake of simplicity, the bore 253 of the punch, when referred to in this specification, should be interpreted to include the bore formed in the body of the punch and the bore formed in the cutting element because the two bores are contiguous.

A free end of the cutting element projects from the cutting end of the punch to form a cutting edge 255a. Preferably, the bore 253 of the punch is cylindrical so that the cutting edge is substantially circular. A sample holding cavity 256 is formed within the projecting wall(s) of the cutting element.

A plunger 257 is held within the bore 253 of the punch and forms part of the collecting device. Optionally, the plunger comprises an RFID device 259 used to identify the origin of the tissue sample held by the collecting means, as shown in FIGS. 7a to 7d. The plunger has a first end 258a and an opposing second end 258b. When the plunger is in an active position, ready for the collecting device to cut a tissue sample, the second end of the plunger projects from the pushing end of the punch and the first end of the plunger is held within the bore of the punch between the sample holding cavity and the pushing end of the punch. The plunger 257 has a slightly smaller diameter to that of the bore 253 of the punch so that the plunger is able to slide back and forth within the bore. Preferably, the first end 258a of the plunger is enlarged.

The collecting device is adapted to cut a sample of tissue from a sample specimen, such as an animal or plant, using the cutting element of the punch, and the sample can temporarily be held within the sample holding cavity. To release the sample from the sample holding cavity, the plunger is adapted to be pushed through the bore of the punch toward the cutting edge and through the sample holding cavity so that the tissue sample is pushed out of the cavity.

Although in a preferred form the punch is substantially tubular and the plunger is substantially cylindrical, it is envisaged that the punch and plunger may be of any suitable complementary shape. For example, the bore of the punch may have a square cross-section and the plunger may also have a square cross-section of a slightly smaller size so that the plunger can slide within the bore of the punch. It should be appreciated that the cutting edge of the cutting element could also be of any suitable shape and size to cut a tissue sample that fits within the storage tube for receiving the sample. For example, the cutting tip may be square, oval, star shaped or irregularly shaped.

When a collecting device 250 is positioned within the magazine housing 200 in the collecting position, the second end of the plunger aligns with the ram receiving aperture 221 and the cutting edge 255a of the cutting element 255 aligns with the cutting region aperture 211, as shown in FIG. 7.

The tube holder 400 of the tissue sampler is adapted to hold a storage tube 500 therein. The storage tube may be any commercially available storage tube that fits within the tube holder. In one form, as shown in FIGS. 9a to 9d, the storage tube 500 comprises a tube body 510 having an open first end 501a and a closed second end 501b, which forms the base of the tube, although it should be appreciated that the tube will not always be oriented so that the base is at the bottom of the tube.

Figure 9C:
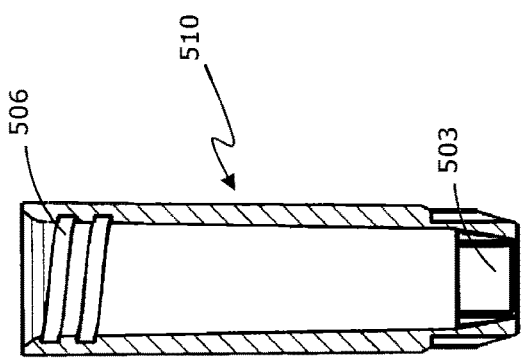
Figure 9B:
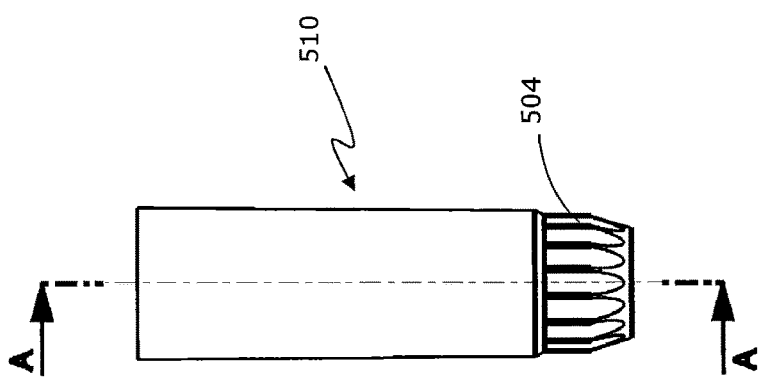
Figure 9D:
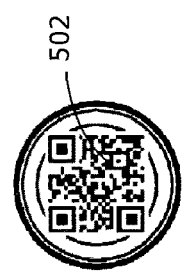
Figure 9A:
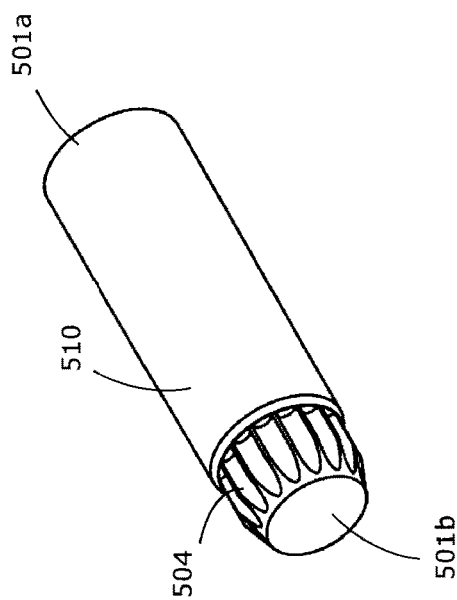
FIG. 9a is a perspective view of one form of storage tube body according to the invention.
Figure 9E:
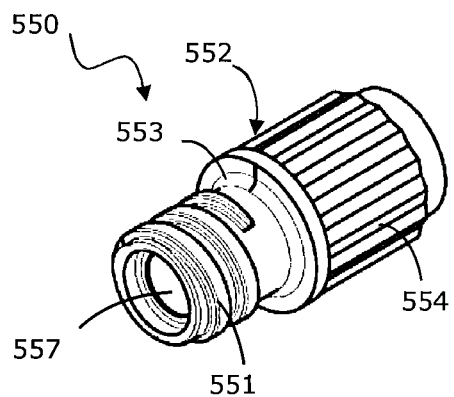
FIG. 9e is a perspective view of one form of cap for a storage tube according to the invention.
Figure 9F:
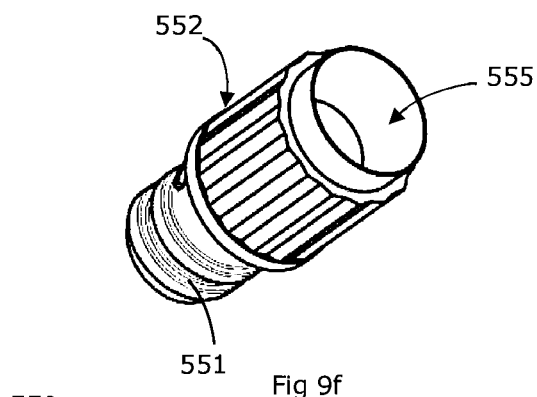
FIG. 9f is another perspective view of the cap of FIG. 9e.
Figure 9G:
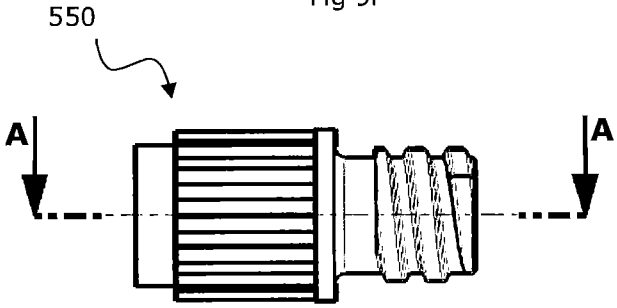
FIG. 9g is a side view of the cap of FIG. 9e.
Figure 9H:
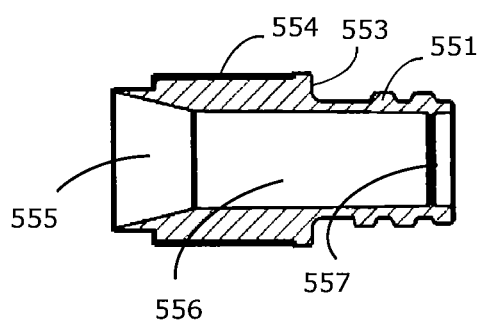
FIG. 9h is a cross-sectional side view of the cap of FIG. 19e.

Optionally, the base of the tube is flat and unique indicia 502, such as a bar code, QR code, matrix code, or the like is provided on the base, as shown in FIG. 9d. Alternatively or additionally, unique indicia is provided along the side of the tube body. The unique indicia is used to provide information about the source of the tissue sample that will ultimately be placed within the tube. In one form, the tube body 510 comprises a tissue chamber 503 at its base to receive a tissue sample. A desiccant or preservative 505 may be provided in the tissue chamber.

Preferably, the outer surface of the tube body comprises anti-rotation means 504 located at or near the base of the tube, as shown in FIGS. 9a to 9d. The anti-rotation means comprise one or more recesses and/or projections adapted to prevent the tube from rotating within a cell of a holding rack, as will be described later in this specification.

When a tissue sample is to be taken, a storage tube 500 is placed in the tube holder 300 so that its first end 501 faces toward the cutting region 400, as shown in FIG. 6.

Optionally, the storage tube comprises a cap that attaches to the open first end of the tube body to seal the tube. Alternatively, the cap may have an aperture formed therein through which a tissue sample can be placed in the storage tube. In this form, the cap is attached to the tube, but does not fully seal the tube.

Preferably, the storage tube body comprises a threaded region at or near its first end that meshes with a threaded region of the cap to allow the cap to be screwed onto and off the storage tube. Alternatively, the cap is attached to the open end of the tube with a snug fit. In yet another form, the cap comprises a lip on its inner surface that nests within a channel that surrounds the outer surface of the tube near the open end of the tube. As will be appreciated, the cap may be attached to the tube in any other suitable arrangement and these are just some examples that could be used.

In one form, as shown in FIGS. 9e to 9h, the storage tube 500 comprises a cap 550 that is screwed onto a threaded region 506 of the tube body 510, as described above. In particular, the cap comprises a threaded shaft 551 that is adapted to engage with a threaded interior region 506 of the tube 500 so that a first end of the shaft projects toward the base 501b of the tube. Alternatively, the shaft may have a threaded bore that is adapted to engage with a threaded exterior region of the tube so that a first end of the shaft projects toward the end of the tube. A collar 552 extends from the opposing second end of the threaded shaft. The collar 552 comprises an outwardly projecting annular flange 553 and a guide wall 554 that extends from the periphery of the flange 553 in a direction away from the shaft 551 to form a substantially cylindrical wall. Preferably, an outer surface of the guide wall is contoured or textured to provide a knurled cap.

A centrally located recess 555 is provided within the collar 552 and between the guide wall. The recess may be specially shaped for engagement with a correspondingly shaped cap-release tool to remove the cap from the tube. For example, the recess 555 may have a tool-engageable edge 559 that provides the recess with a cruciform shape, star shape, hex shape, square shape, oval shape, or any other regular or irregular shape that corresponds to the shape of a tool for inserting into the recess and turning the cap to unscrew the cap from the tube body. However, it is preferred that the outer surface of the guide wall is shaped to correspond with the shape of a tool, or to at least provide a gripping region, for gripping the outer wall and turning the cap to decap the storage tube.

The recess 555 aligns with a bore 556 that is centrally located within the cap. The cap also comprises a breakable seal 557, which may be in the form of a membrane, or the like, that extends laterally across the cap. The seal may be formed integrally with the collar and shaft of the cap so that the entire cap is made as one part. Preferably, the seal is located at or near a first end of the shaft, but in other forms, the seal may be located within the collar of the cap or in any other suitable location. The seal 557 may be of any suitable material, such as polypropylene, rubber, polyethylene, or the like. When the cap 550 is attached to the body of a storage tube 510 so that the first end of the shaft projects into the tube body, the seal 557 extends across the body of the tube to seal the first end 501a of the tube body. Preferably, the cap 550 also comprises a second seal 558, such as an o-ring, that fits over the outside of the threaded shaft 551 and abuts the collar 552 of the cap. In this form, when the cap is attached to the body of a storage tube, the second seal is positioned between the first end 501a of the tube body and the collar 552 of the cap 550 to seal the connection between the cap and the tube. In this arrangement, the cap can be screwed onto a sterile tube to hermetically seal the tube. The tube can remain sterile until the seal is broken and a tissue sample is placed in the storage tube.

Preferably, the cap includes a tamper evident closure that indicates when the seal between the cap and storage tube has been broken so that the storage tube might no longer be sterile. For example, connecting tabs may be provided between the collar and an attachment ring of the cap that is securely attached to the tube. In this form, if the cap is twisted away from the attachment ring (such as by unscrewing the cap from the tube), the connecting tabs break to indicate that the storage tube has been tampered with.

Figure 10:
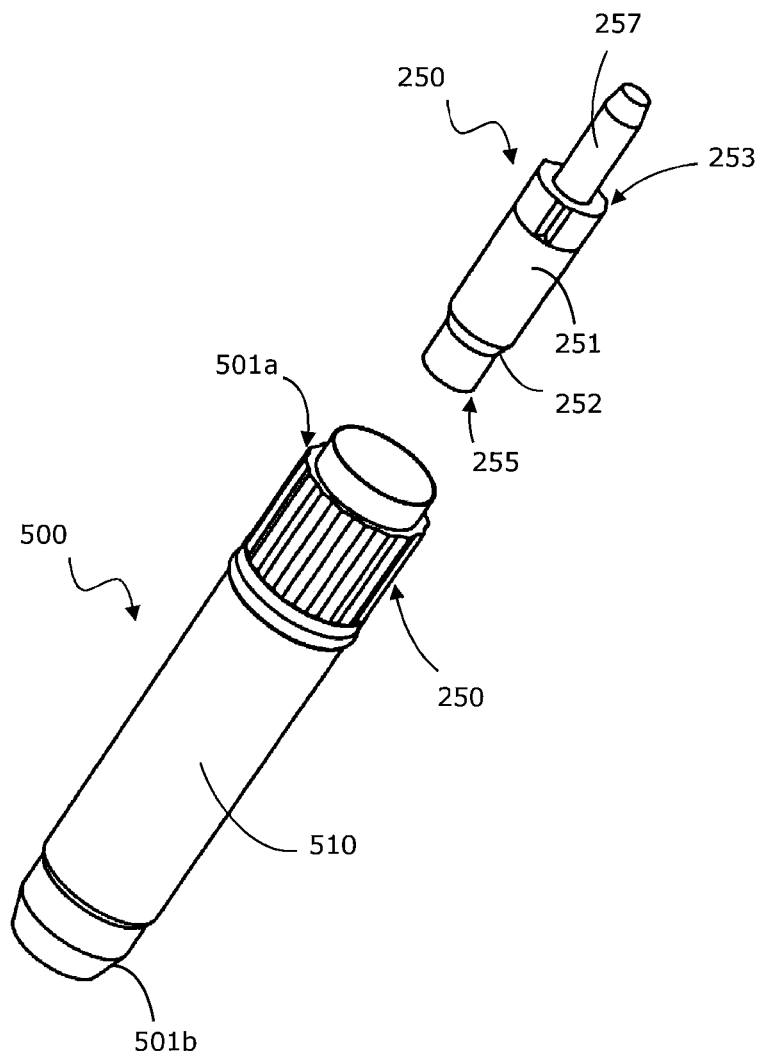
FIG. 10 is a schematic perspective view of one form of collecting device of the invention before being inserted into a storage tube.
Figure 11:
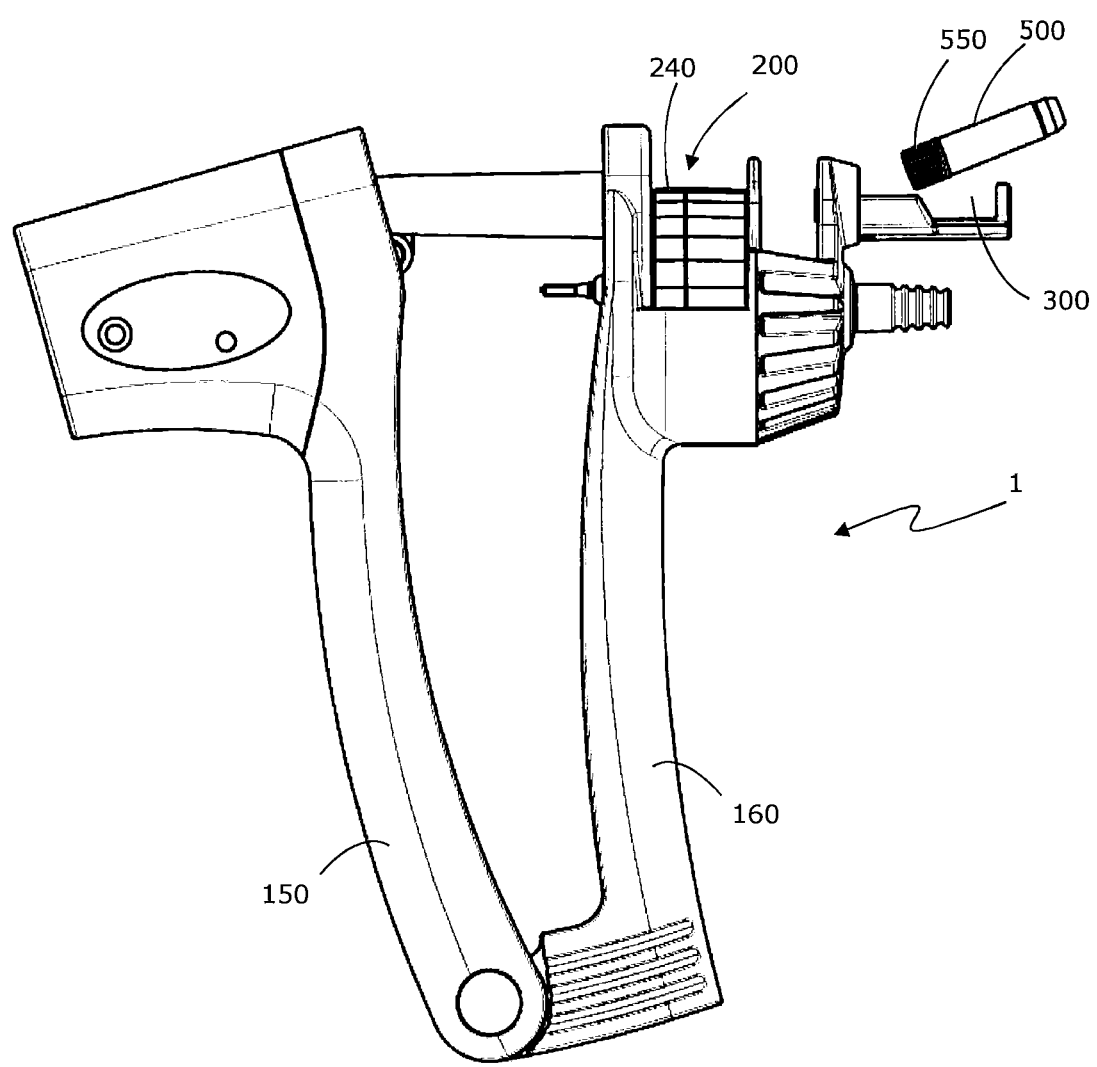
FIG. 11 is a side view of one form of tissue sampler according to the invention in which a storage tube is about to be placed into the tissue sampler.
Figure 12:
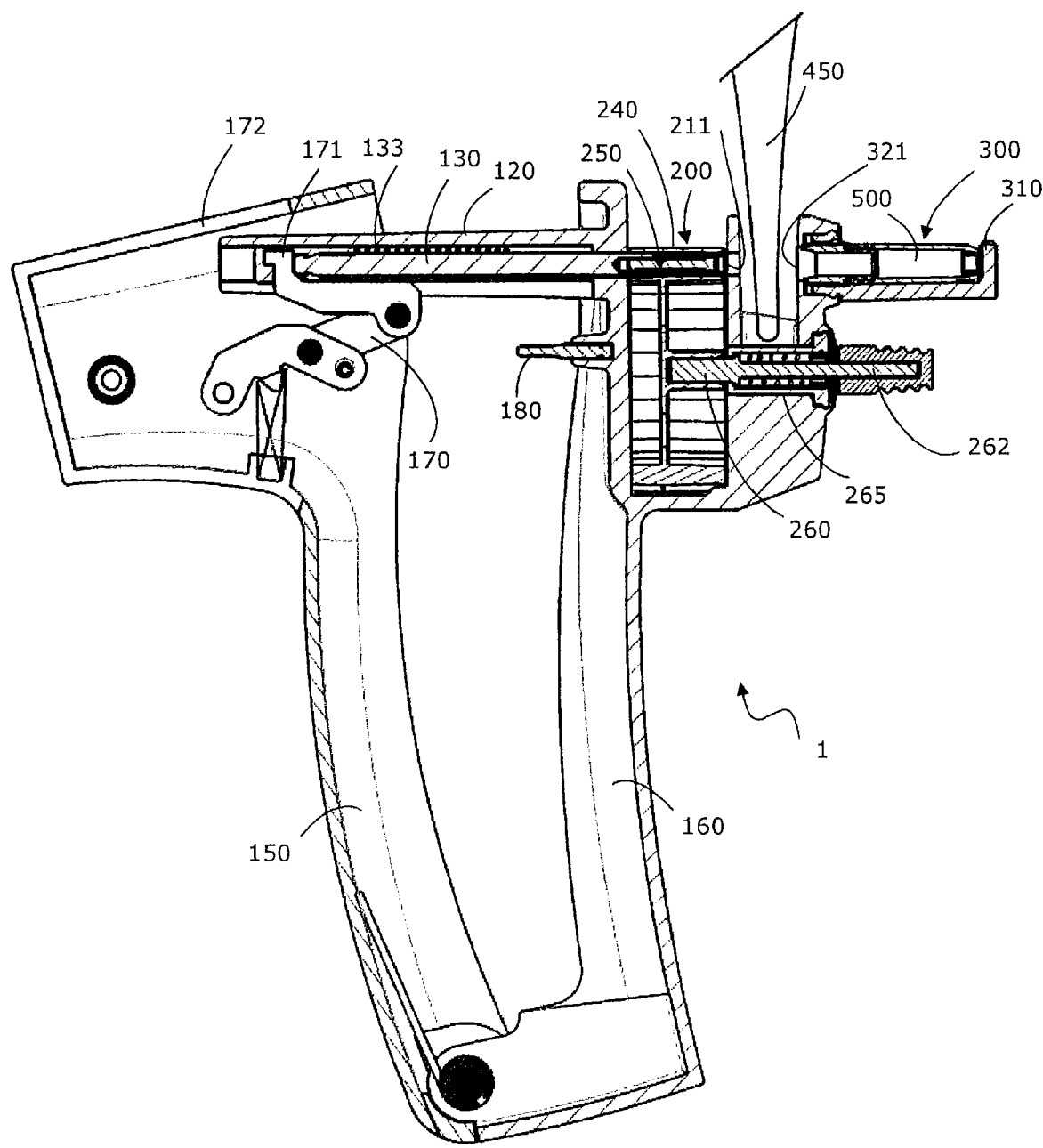
FIG. 12 is a cross-sectional side view of the tissue sampler of FIG. 11 in which an animal's ear is located in the cutting region.

The storage tube (including cap) is dimensioned to fit within the tube holder of the tissue sampler, as shown in FIGS. 11 and 12 and to receive a collecting device through the first end of the storage tube, as indicated in FIG. 10.

As shown in FIG. 1a to 1c and FIG. 11, the storage tube holder 300 comprises a front wall 310, a rear wall 320, and a supporting wall 330 extending between the front and rear walls. The front, rear and supporting walls are adapted to hold a storage tube 500. Preferably, the supporting wall is a bottom wall and the front, rear, and bottom walls are adapted to form a cradle within which a storage tube can be held.

The rear wall 320 of the tube holder 300 comprises a sample receiving aperture 321 that connects to the cutting region and through which a portion of a storage tube can be located. In one form, when a storage tube 500 is held in the tube holder 300, a portion of the storage tube (i.e. the open first end of the tube or the cap, as the case may be) is located within the sample receiving aperture 321 and the first end 501a of the storage tube projects slightly into the cutting region to form an anvil against which tissue is pressed during a cutting operation. In another form, the storage tube is located between the front and rear walls of the tube holder and is positioned so that the first end of the tube aligns with the sample receiving aperture.

The sample receiving aperture 321 aligns with the cutting region aperture 211 formed in the front wall of the magazine housing, as shown in FIGS. 12 to 17.

Figure 13:
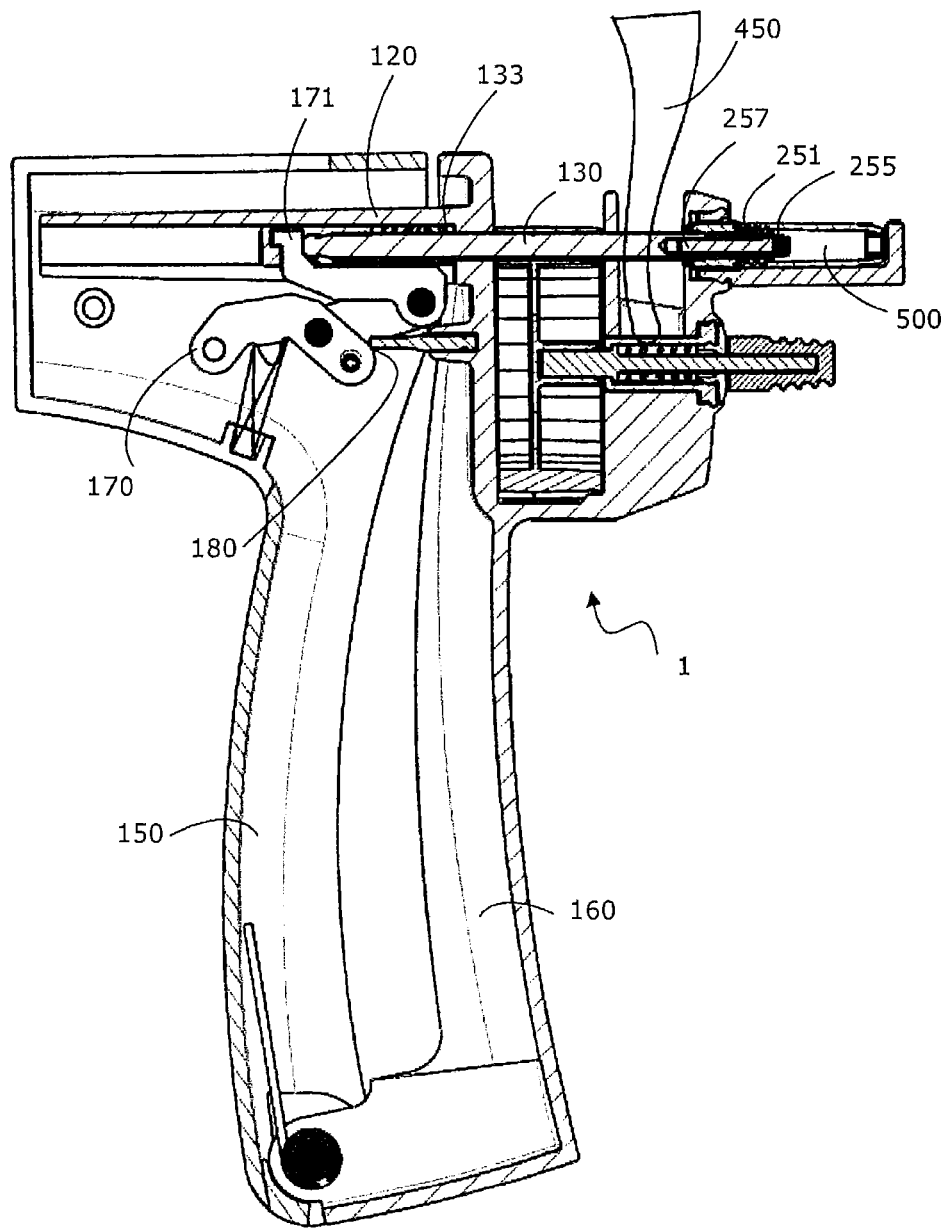
FIG. 13 is a cross-sectional side view of the tissue sampler of FIG. 12 in which a tissue sample has been cut from the animal's ear.
Figure 14:
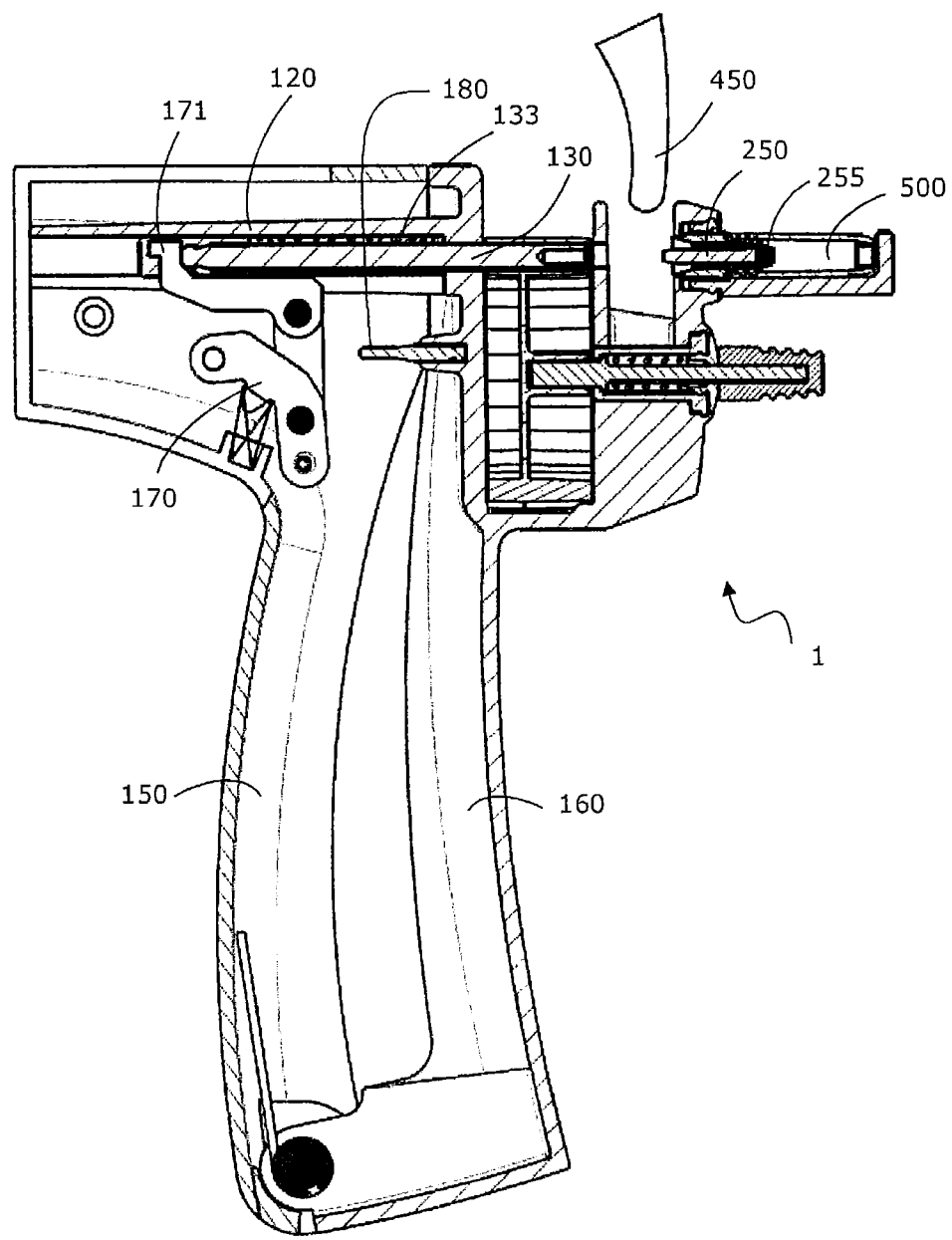
FIG. 14 is a cross-sectional side view of the tissue sampler of FIG. 13 in which the animal's ear is removed from the cutting region and the collecting device plugs the first end of the storage tube.
Figure 15:
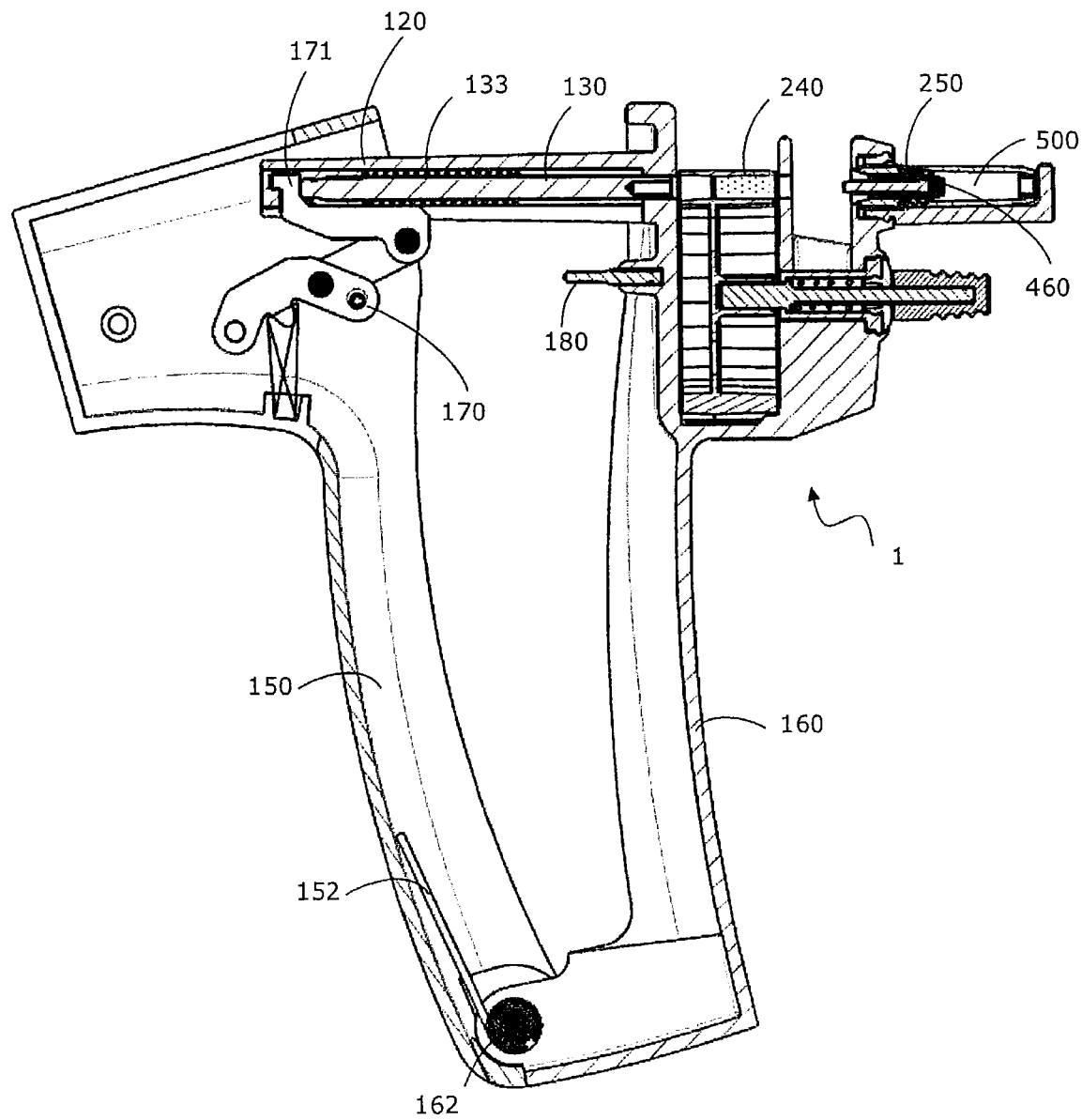
FIG. 15 is a cross-sectional side view of the tissue sampler of FIG. 14 in which the ram has been retracted through an empty chamber of the collecting device magazine and is returned to its rest position.

As shown in FIGS. 1a to 1c, the cutting region 400 is positioned between the rear wall 320 of the tube holder 300 and the front wall 210 of the magazine housing 200. The cutting region 400 comprises a space in which tissue 450 from a sample specimen can be positioned. In FIGS. 13 to 15, an animal's ear 450 is schematically shown positioned within the cutting region. The ear, or other item, is kept in the cutting region as a tissue sample is cut from the ear.

A first end of a ram housing 120 connects to the ram receiving aperture 221 located on the rear wall of the magazine housing.

A ram 130 is positioned within the ram housing 120. The ram forms part of an actuating means, which also comprises a trigger 150 operably connected to the ram 130. In particular, a first end 131a of the ram rests within a first end 121a of the ram housing and proximate to the ram receiving aperture 221. A guiding recess 132 is formed in the first end of the ram and is shaped to correspond with the second end 258b of the plunger, which projects from the punch. The guiding recess 132 is dimensioned so that the projecting portion of the plunger can fit within the recess and so that the first end of the ram 121a can abut the pushing end 252b of the punch. A second end 131b of the ram rests within a second end 121b of the ram housing and is operably connected to the trigger 150. The ram 130 is adapted to slide back and forth within the ram housing 120 as the trigger 150 is engaged and disengaged.

In one form, as shown in FIGS. 1a to 1c, the second end of the ram housing comprises an actuator aperture 122 through which an actuator linkage 170 engages with the ram 130 to connect the ram to the trigger 150. In one form, the actuator linkage 170 comprises a pusher 171 that is adapted to push the second end 131b of the ram toward the magazine housing 200 when the trigger is engaged. Preferably, the pusher is attached to the second end of the ram, as shown in FIGS. 1c and 13 to 18. In another form, not shown, the linkage is attached to the ram to pull the second end of the ram toward the magazine housing when the trigger is engaged.

As shown in FIGS. 1c and 12 to 17, the trigger 150 forms part of the handle of the tissue sampler 1. The handle also comprises a gripping member 160 having a first end 161a that extends from the body 100 of the sampler 1. An opposing second end 161b of the gripping member is pivotably attached to a second end 151b of the trigger via a pivot pin 162, as shown in FIG. 1c. In this arrangement, the trigger can pivot about the second end of the gripping member as a first end 151a of the trigger moves toward and away from the first end 161a of the gripping member.

When the trigger is in a disengaged position, the first end of the trigger is spaced away from the first end of the gripping member. Conversely, when the trigger is in an engaged position, the first end of the trigger is squeezed toward the first end of the gripping member. In a preferred form, the trigger is biased to the disengaged position by a trigger biasing member 152, which may be a spring pin as shown in FIG. 1c, a compression spring, or any other suitable biasing means.

A linkage housing 172 is provided at the first end 151a of the trigger 150. The linkage housing is adapted to house the linkage 170 that connects the trigger 150 to the ram 130 and to at least partially surround the ram housing 120 also. In the embodiment shown in FIGS. 1c and 6, a first end of the linkage attaches to the linkage housing via a biasing means, preferably in the form of a linkage compression spring 173, which pushes the linkage upward toward the ram housing. A second end of the linkage engages with the ram, as described above. However, in alternative forms, the first end of the linkage may be attached to the tissue sampler at any suitable location.

In one form, the linkage 170 is an over-centre linkage that comprises a pivoting arm 174, a pusher 171 (as described above), and a connecting arm 175 that connects the pivoting arm to the pusher. The pivoting arm 174 is substantially shaped like an inverted U, one arm of which is pivotably attached to the trigger housing at a first off-centre pivot point 174a and is also pivotably attached to a first end of the connecting arm at a second off-centre pivot point 176. The opposing second end of the connecting arm is pivotably attached to the pusher a second pivot point 177. The linkage also comprises a stop 174b that is attached to the pivoting arm and that pushes against a lower edge of the connecting arm to lock the linkage in an over-centre rest position.

A striker 180 projects from a rear wall 111 of the body of the tissue sampler and toward the linkage. The striker and linkage are adapted so that when the trigger reaches the engaged position, the pivoting arm of the linkage, which has extended toward the body of the tissue sampler, pushes against the striker, which trips the linkage so that it automatically returns to its over-centre rest position.

In one form, a ram biasing means biases the ram toward a rest position in which the ram lies substantially within the ram housing. In the embodiment shown in FIG. 1c, the ram biasing means 133 is a compression spring that surrounds the second end of the ram 130 and is positioned between the pusher 171 and a front wall 123 of the ram housing 120. Preferably, in the rest position, the spring is merely floating and has no biasing effect until the actuating means is engaged, at which time the pusher pushes the ram toward the magazine housing and pushes against the spring to compress the spring against the front wall of the ram housing. In another form, an outwardly projecting collar may be provided at or near the second end of the ram so that the collar compresses the spring against the front wall of the ram housing when the actuating means is engaged.

Because the biasing means biases the ram to its rest position, when the trigger is in the engaged position, the linkage is tripped by the striker and the compressed spring 133 pushes against the pusher 171 or against the collar of the ram, as the case may be, to return the ram 130 to the rest position within its housing.

In particular, as the linkage pushes against the striker, the pivoting arm 174 is pushed downwards, compressing the linkage biasing spring 173. Once the pivoting arm moves past a centre line between pivots 177 and 174a, it becomes over-centre and the ram biasing spring 133 drives the ram 130 back into its rest position in the ram housing and simultaneously forces the linkage to the unlocked position, as shown in FIG. 14, in which the stop 174b no longer presses against the lower edge of the connecting arm. Therefore, by releasing the trigger 150 so that the trigger biasing pin 152 pushes the trigger to the disengaged position, as shown in FIG. 6, the ram compression spring 133 is decompressed, allowing the linkage spring 173 to return the linkage back over-centre to the locked over-centre rest position shown in FIG. 6.

FIGS. 12 to 17 illustrate the position and/or movement of the actuating means, the collecting device, and the storage tube as a tissue sample is taken using the tissue sampler of the invention. FIGS. 19 to 24 illustrate the position and/or movement of the collecting device and storage tube of the invention as a tissue sample is taken.

The invention also relates to a method of cutting a tissue sample using the tissue sampler and collecting device of the invention. To cut a tissue sample, a user inserts a storage tube 500 into the tube holder 300 so that a portion of the storage tube is pushed into the sampler receiving aperture 321 so that the first end of the storage tube projects slightly from the sample receiving aperture 321 and into the cutting region, as shown in FIG. 12. The locator release pin 262 is pulled to retract the spindle 260 from the magazine housing 200 and a collecting device magazine 240 is placed within the magazine housing. The locator release pin 262 is then returned to its rest position so that the spindle 260 projects through the bore 242 of the magazine. The magazine 240 is orientated so that the cutting edge of the punch 251 of the active collecting device 250 is aligned with the cutting region aperture 211 and the second end of the plunger 257 is aligned with the ram receiving aperture 221. As will be appreciated, the collecting device magazine can be placed into the tissue sampler before or after the storage tube is placed in the tissue sampler.

The user then holds the handle of the tissue sampler and positions the sampler so that the tissue 450 to be sampled (such as an animal's ear) is located in the cutting region 400, as shown in FIG. 12. The user squeezes the trigger 150 toward the gripping member 160 to move the trigger from the disengaged position to the engaged position. As the trigger pivots about the pivot pin 162 so that the first end of the trigger moves toward the first end of the gripping member, the linkage 170 is pulled in the same direction, causing the ram 130 to slide along the ram housing 120 toward the active collecting device 150.

The ram moves through the ram receiving aperture and pushes against the second end of the plunger of the active collecting device. The ram continues pushing on the plunger to push the collecting device out of the chamber of the magazine, through the cutting region aperture, into the cutting region, and toward the storage tube. The movement of the ram toward the storage tube compresses the previously floating spring against the front wall of the ram housing.

Figure 19:
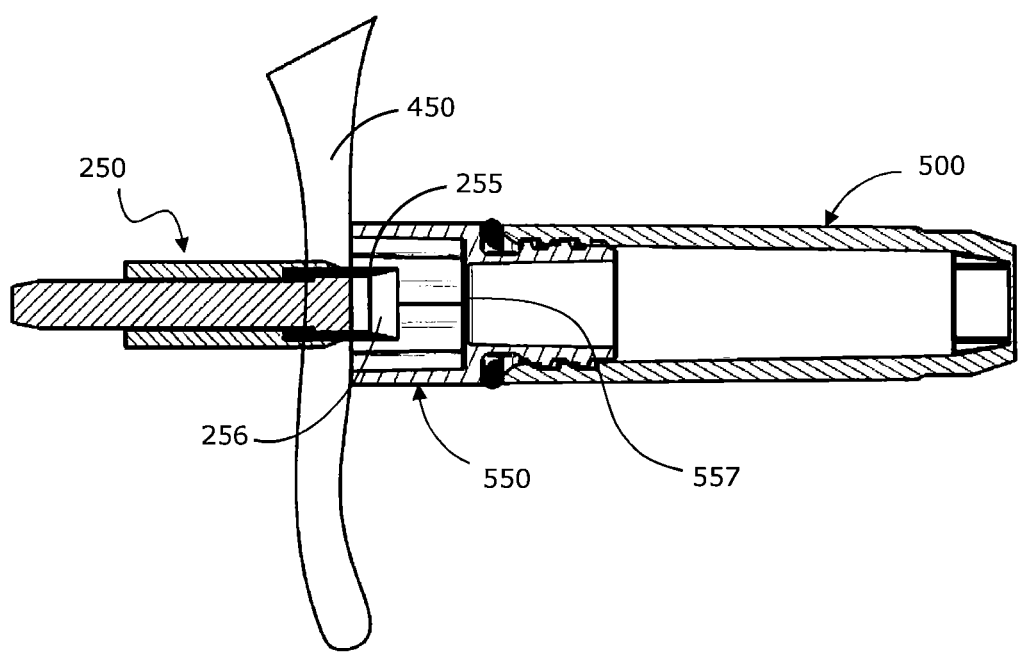
FIG. 19 is a cross-sectional side view of the collecting device of FIG. 18 when cutting a tissue sample from the animal's ear.
Figure 20:
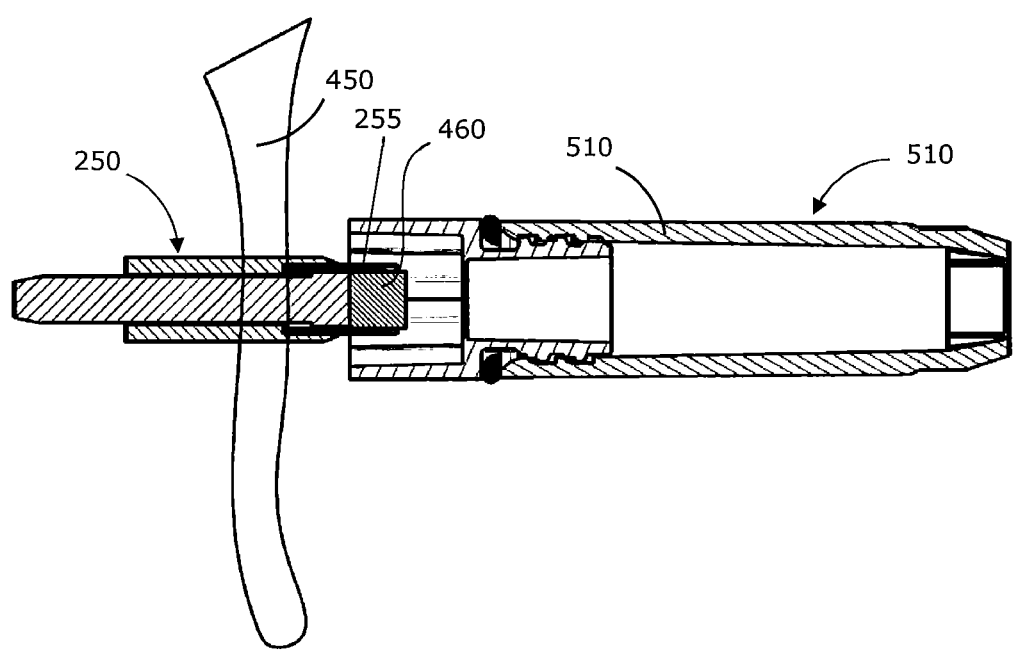
FIG. 20 is a cross-sectional side view of the collecting device of FIG. 19 after a tissue sample has been cut.
Figure 21:
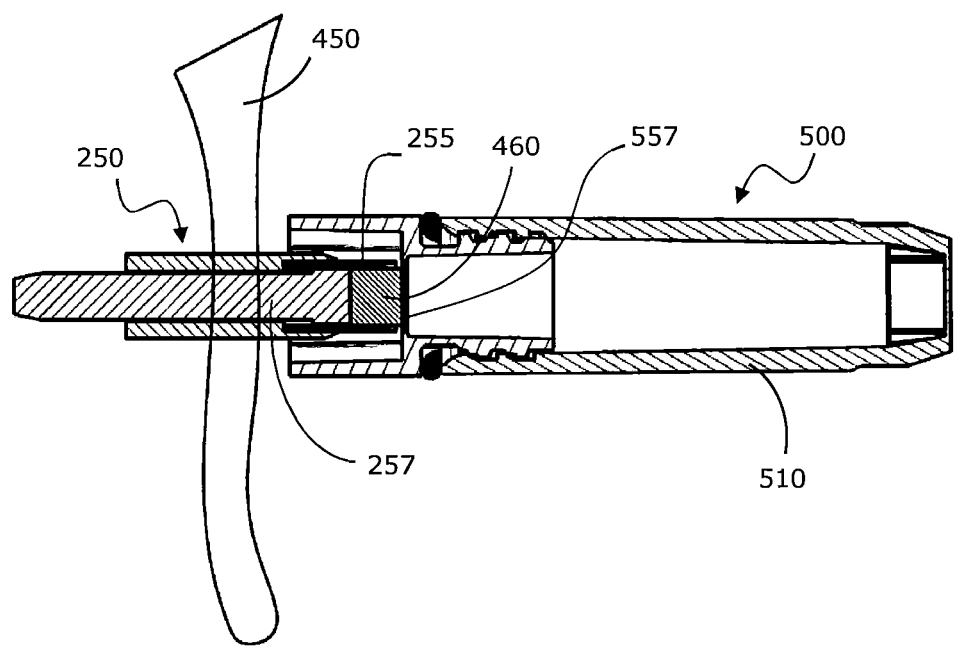
FIG. 21 is a cross-sectional side view of the collecting device of FIG. 20 pressing against a membrane in the cap of the storage tube according to one aspect of the invention.
Figure 22:
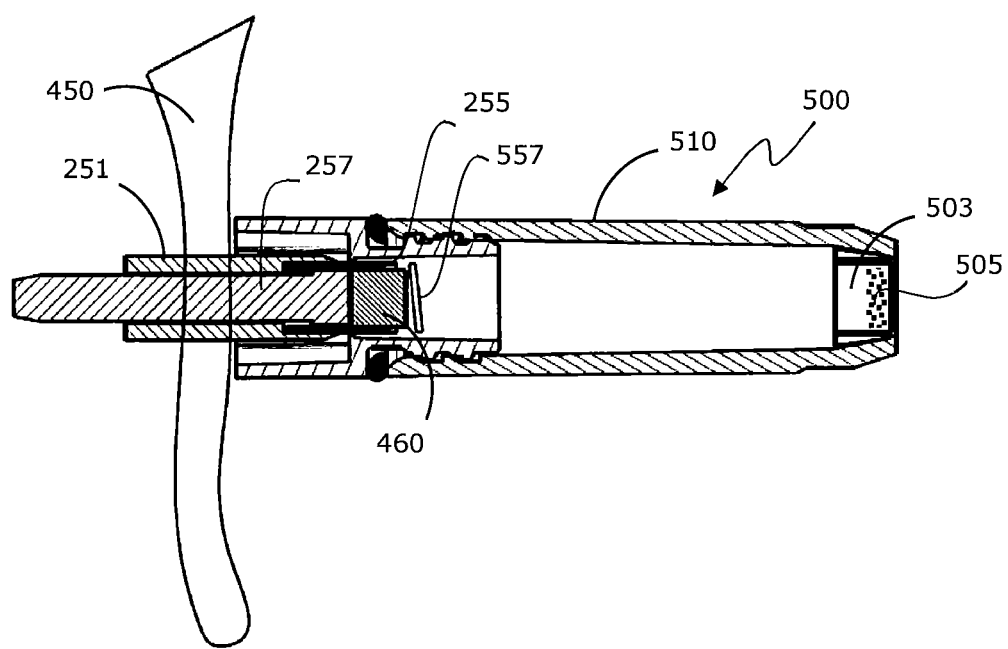
FIG. 22 is a cross-sectional side view of the collecting device of FIG. 21 after the membrane has been broken.
Figure 23A:
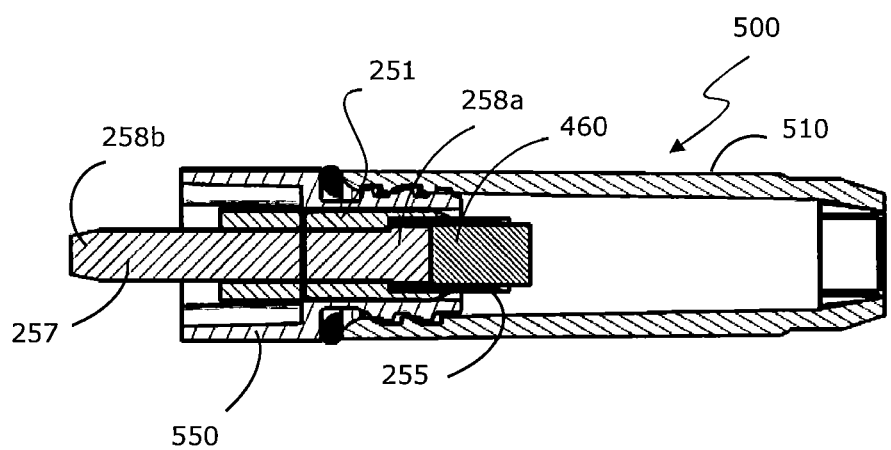
FIG. 23a is a cross-sectional side view of the collecting device of FIG. 22 in which the collecting device is plugging the first end of the storage tube.
Figure 23B:
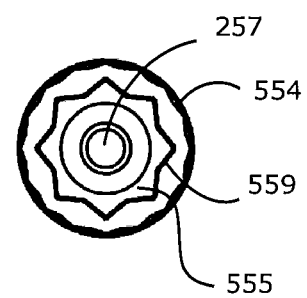
FIG. 23b is an end view of the collecting device within the cap of the storage tube.

As the ram pushes the collecting device through the cutting region, the cutting end of the punch pushes the animal's ear (or other tissue) against the first end of the storage cap and the first wall of the cutting region. The cutting edge of the punch is then pushed through the ear or other tissue to cut a sample plug from the tissue, as shown in FIGS. 13 and 19.

It is not essential that a collecting device having a punch and a plunger sliding within a bore of the punch (as described above) is used with the tissue sampler of the invention. Where the collecting device is used with a different form of tissue sampler, the punch of the collecting device may push the tissue/ear directly against the first end of a storage tube before cutting a sample plug, as shown in FIGS. 19 to 22. The tissue sample is held within the sample holding cavity of the collecting device and the collecting device is pushed into the first end of the storage tube to place the sample within the tube.

In particular, and returning to the tissue sampler of the invention, as the trigger 150 is further squeezed toward the gripping member 160, the collecting device 250 is pushed further forward by the ram 130 and through the first end of the storage tube projecting from the sample receiving aperture 321.

As shown in FIGS. 15 to 24, where the first end of the storage tube 500 comprises a cap 550 with a seal 557 as described above, the collecting device 250 is pushed into the recess 555 formed in the cap. Optionally, the wall of the recess comprises one or more ribs for engaging with the guiding ribs 254 of the punch to guide the body of the punch within the cap. As the collecting device pushes into the cap, the cutting edge 255a of the punch presses against and then pierces the seal or membrane 557 to form an opening to the storage tube body. The cutting end of the punch (holding the plunger therein) is then pushed through the opening so that the sample holding cavity 256, and the sample 460 held within the cavity 256, is located within the body of the storage tube 500. The collecting device fills the opening formed by the broken seal to close off the first end of the tube. In particular, the diameter of the punch is sized to fit snugly within the opening formed in the cap so that the cap is able to hold the collecting device therein. Preferably, the second end of the plunger projects from the pushing end of the punch and the first end of the plunger is located within the bore of the punch between the sample holding cavity and the pushing end of the punch. In this arrangement, the plunger can be depressed and pushed through the sample holding cavity to release the tissue sample into the storage tube, as described later in this specification.

In the tissue sampler, the front wall 310 of the tube holder acts as a stop to hold the storage tube 500 in position as the punch 251 pushes against the seal 557 of the cap and into the tube.

When the collecting device closes off the first end of the storage tube, the punch and the plunger are held within the cap of the storage tube so that the cutting element is held within the tube body. It is therefore not necessary for the user to handle the punch with its sharp cutting edge or to otherwise remove and discard the punch from the tissue sampler.

The tissue sampler is adapted so that, at the point at which the collecting device seals the storage tube, the trigger 150 reaches its engaged position and the over-centre linkage 170 is caused to push against the striker 180. The striker and ram biasing means 133 trip the linkage over centre, as shown in FIG. 14. When the linkage returns to its over-centre rest position, the ram biasing means returns to its floating position and the ram is retracted back into the ram housing so that the animal's ear (or other tissue being sampled) can be automatically released. The trigger can also be released so that the force of the trigger biasing means 152 pushes the first end of the trigger away from the gripping member so that the trigger returns to its disengaged position. In this way, the over-centre linkage and striker provide a quick release mechanism that automatically activates when the sample is safely held in the storage tube. Consequently, the action of cutting the tissue sample, placing the sample in the storage tube, and releasing the animal's ear is almost instantaneous so that if the animal reacts to having its ear cut and pulls away, there is little chance that the animal can pull the tissue sampler from the user's hand before the ear is released.

Therefore, the tissue sampler allows for a tissue sample to be cut and placed in a storage tube, for the punch and plunger to seal the storage tube, for the animal's ear to be released, and for the actuating ram to return automatically to its rest position by squeezing the trigger toward the gripping member in a single movement until it reaches the engaged position.

Figure 16:
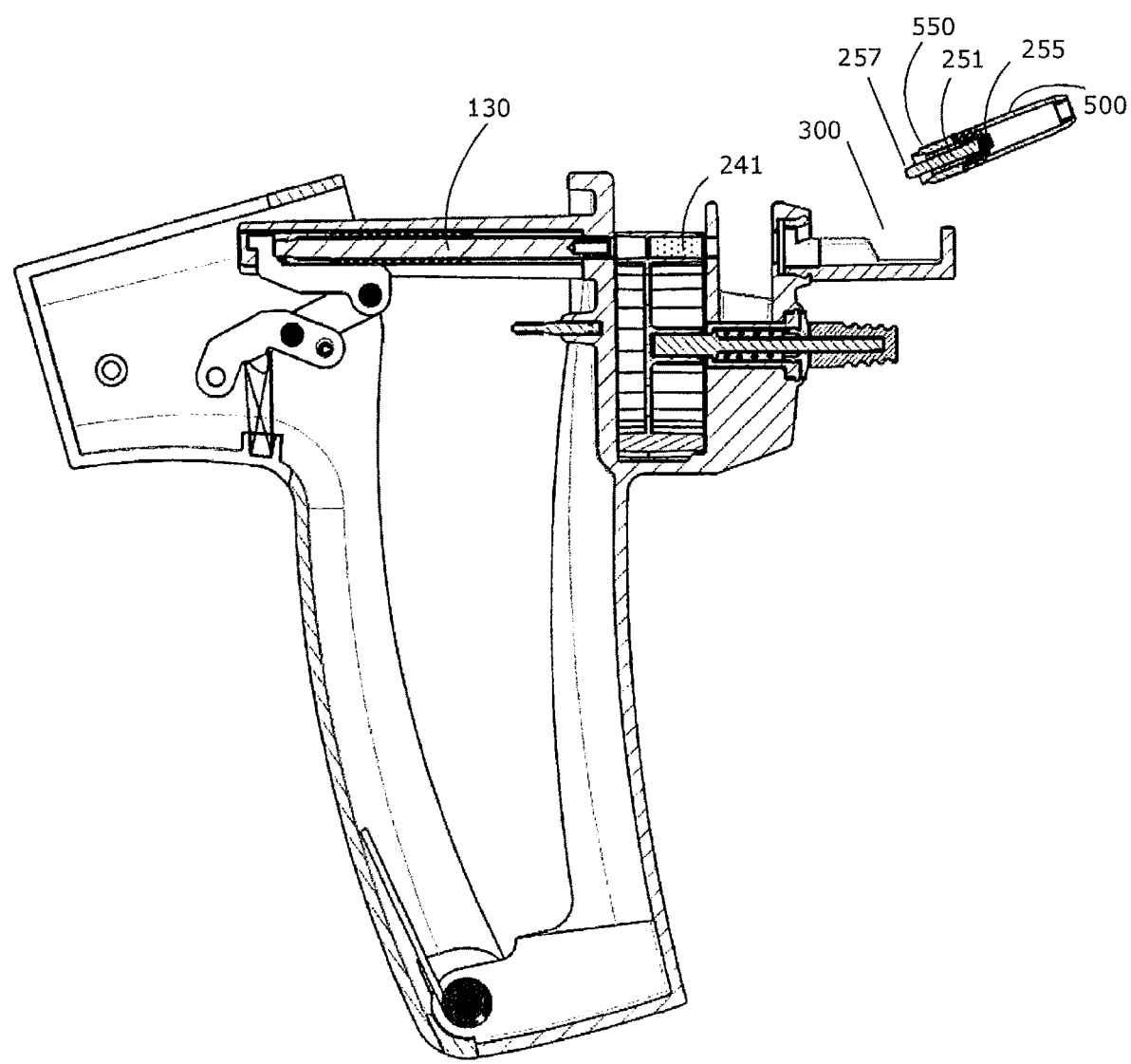
FIG. 16 is a cross-sectional side view of the tissue sampler of FIG. 15 in which the storage tube containing a tissue sample and collecting device is being removed from the sampler.

When the linkage 170 returns to its over-centre rest position and the ram 130 is retracted through the now empty chamber 241 of the magazine and back into the ram housing 120, detritus, such as hair or flesh left over from the sampling operation, will be pulled off the ram and taken into the empty chamber, as shown in FIGS. 15 and 16.

The storage tube, including the cap holding the collecting device can then be removed from the tube holder and an unused replacement storage tube can then be fitted into the tube holder as described above. The collecting device magazine is rotated incrementally until the next chamber containing an unused collecting device is aligned with the ram receiving aperture and cutting region aperture, ready for another tissue sample to be taken.

Figure 17:
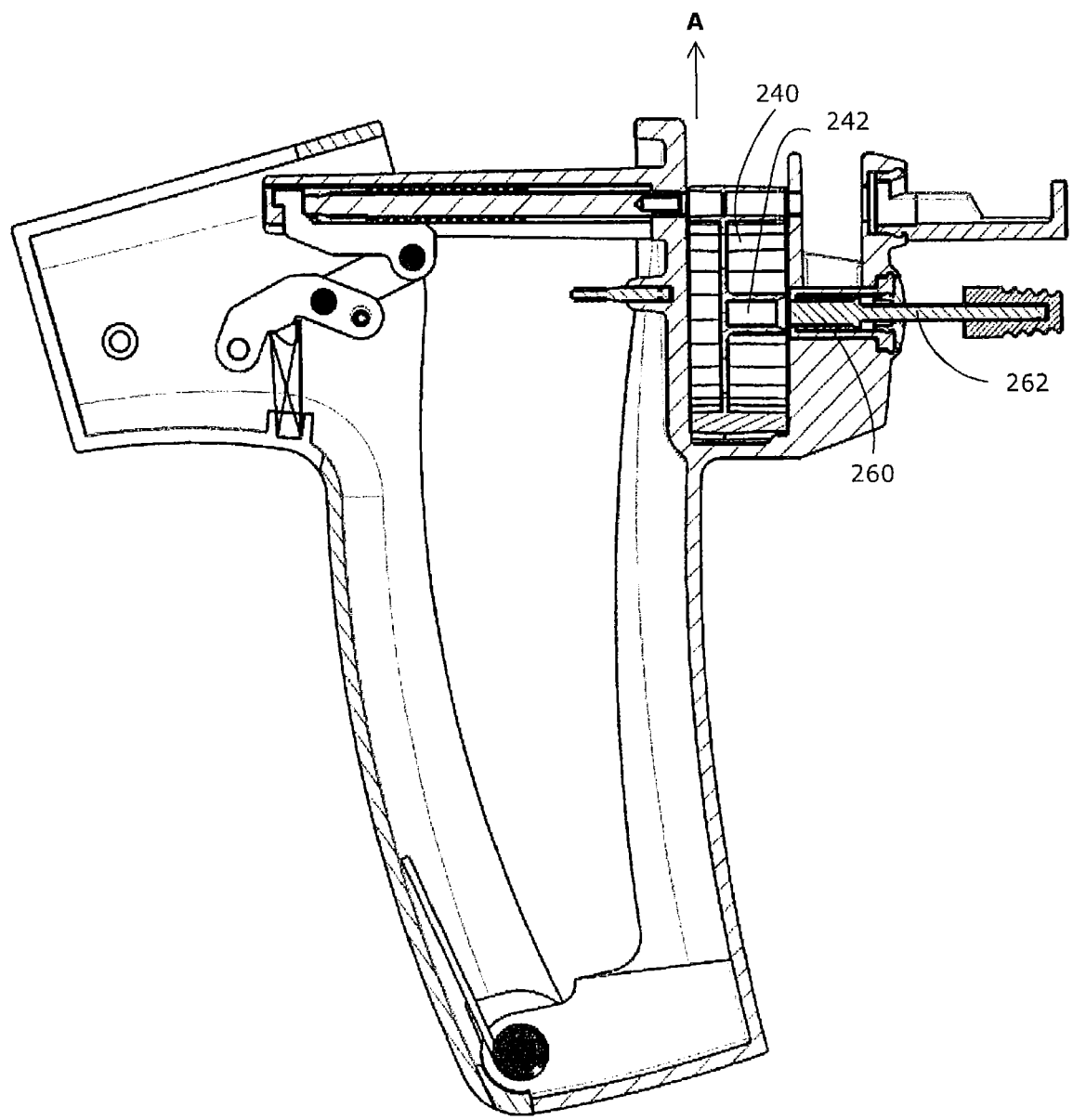
FIG. 17 is a cross-sectional side view of the tissue sampler of FIG. 16 in which the collecting device magazine is about to be removed from the tissue sampler.
Figure 18:
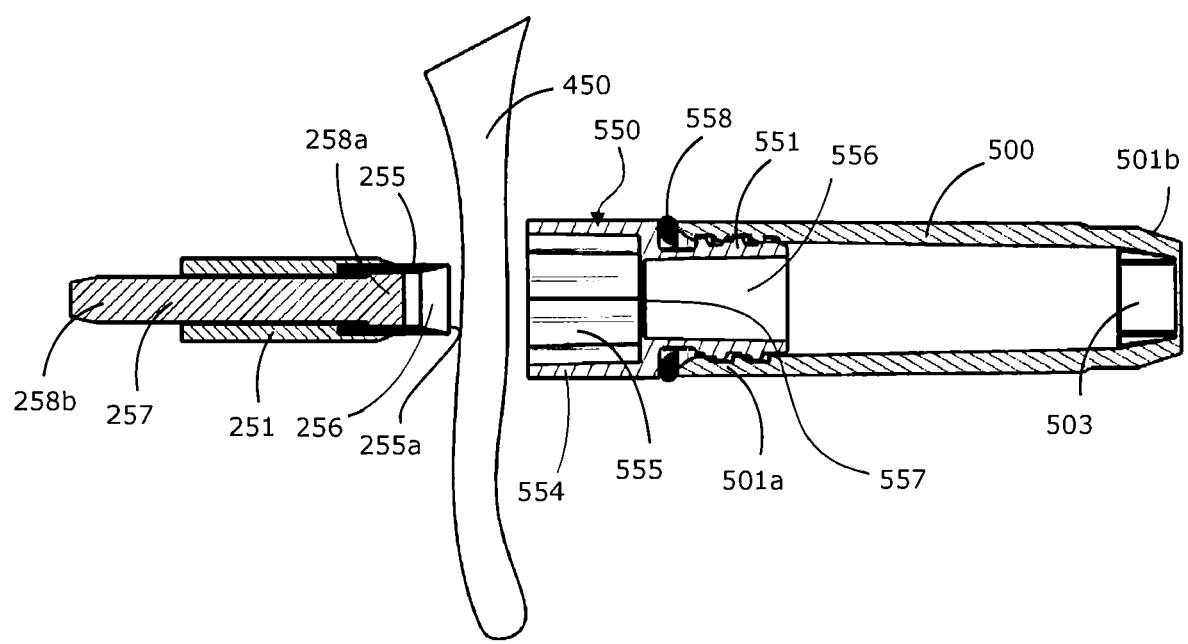
FIG. 18 is a cross-sectional side view of one form of collecting device according to the invention before taking a tissue sample from an animal's ear and placing it into a storage tube.

Once all the collecting devices in the magazine have been used, the locator release pin can be retracted to retract the spindle from the central bore of the magazine, against the bias of the locator compression spring 263 to allow the magazine to be removed, as indicated by arrow A in FIG. 17.

Therefore, the invention also relates to a method of taking a tissue sample using the tissue sampler of the invention. The method comprises the steps of: (a) positioning a collecting device magazine within the magazine housing of the tissue sampler, the collecting device magazine comprising at least one collecting device within a chamber of the magazine; (b) positioning the magazine within the magazine housing to align the at least one collecting device with the ram receiving aperture and with the cutting region aperture; (c) positioning a storage tube within the storage tube holder of the tissue sampler; (d) positioning an item from which a tissue sample is to be taken in the cutting region of the tissue sampler; and (e) engaging the actuating means to cause the collecting device to push through the item to cut a tissue sample and to push into a first end of the storage tube to position the tissue sample within the storage tube, wherein the collecting device is then held within the first end of the storage tube to close off the storage tube. Steps (a), (b), and (c) can be carried out in any order. Preferably, the tissue sample is taken from an animal's ear.

The invention also relates to a method of cutting and placing a tissue sample within a storage tube, the method comprising the steps of: providing a collecting device comprising a punch having a cutting edge and providing a storage tube having a cap comprising a membrane to seal a first end of the cap; pushing the cutting edge of the punch through an item from which a tissue sample is to be taken so that the punch cuts a sample of tissue from the item and holds the tissue sample within the punch; and pushing the punch through the membrane to place the tissue sample within the storage tube, wherein the punch is held within the first end of the storage tube to close off the first end of the tube. In a preferred form, the collecting means further comprises a plunger that slides within a bore of the punch.

Figure 27:
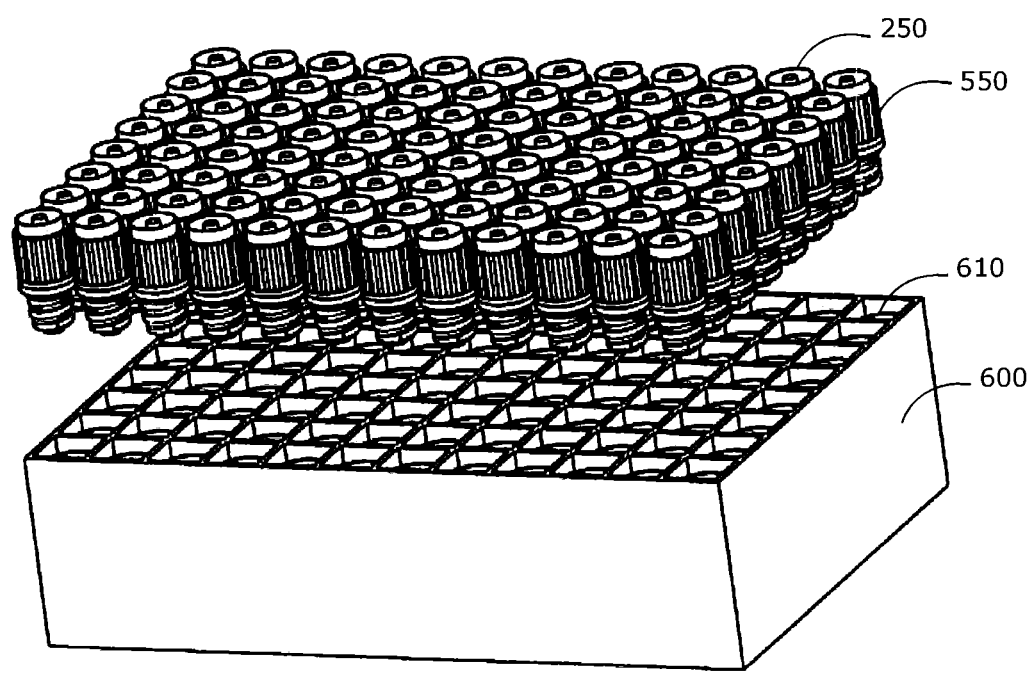
FIG. 27 is a schematic perspective view showing a plurality of storage tubes being decapped simultaneously.
Figure 28A:
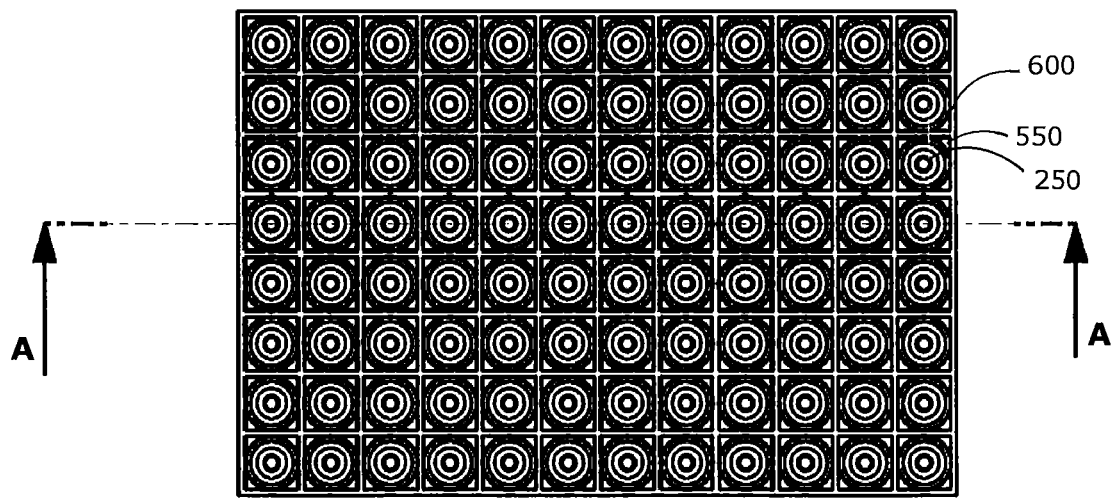
FIG. 28a is top view of the decapped storage tubes of FIG. 27.
Figure 28B:
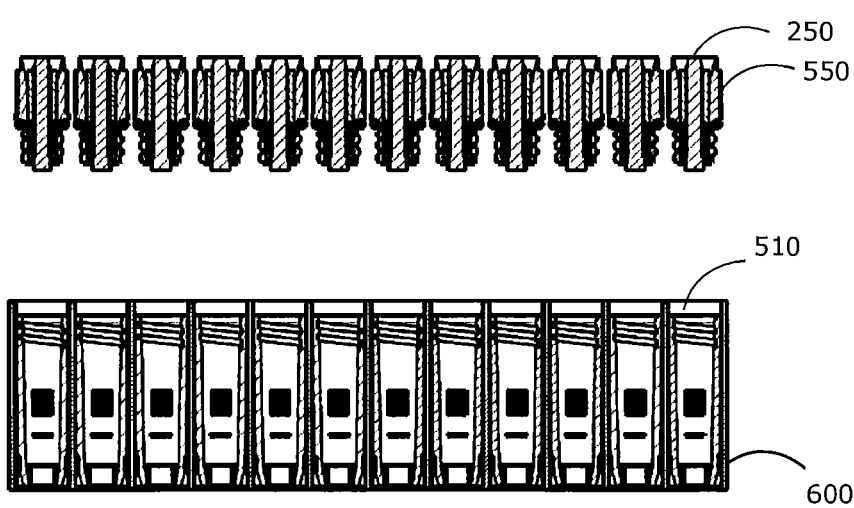
Figure 28C:
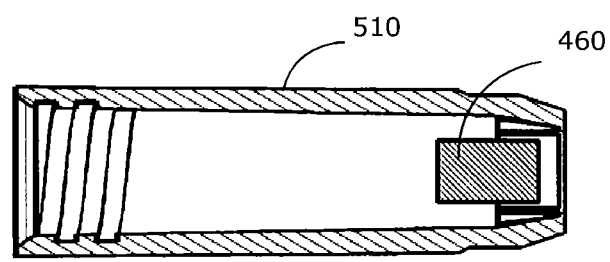
FIG. 28c is a cross-sectional side view of a single storage tube after being decapped.

Preferably, the storage tubes removed from the tissue sampler are placed within respective cells 610 of a multi-cell rack 600, such as a 96 well rack as shown in FIG. 27, before being sent to a laboratory for decapping and future analysis of the samples.

The collecting device is adapted so that the plunger can be pushed through the bore of the cutting element to release the tissue sample from the sample holding cavity and into the tissue chamber at the bottom of the tube. In particular, the second end of the plunger can be depressed toward the pushing end of the punch to cause the first end of the plunger to push a tissue sample out of the sample holding cavity and into the body of the storage tube. To assist with the release of the tissue sample, the first end of the plunger may be enlarged and may comprise an anti-stick surface formed of a non-stick material, such as Teflon™. The plunger may be depressed and pushed into the sample holding cavity after the tube has been removed from a tissue sampler.

Figure 24:
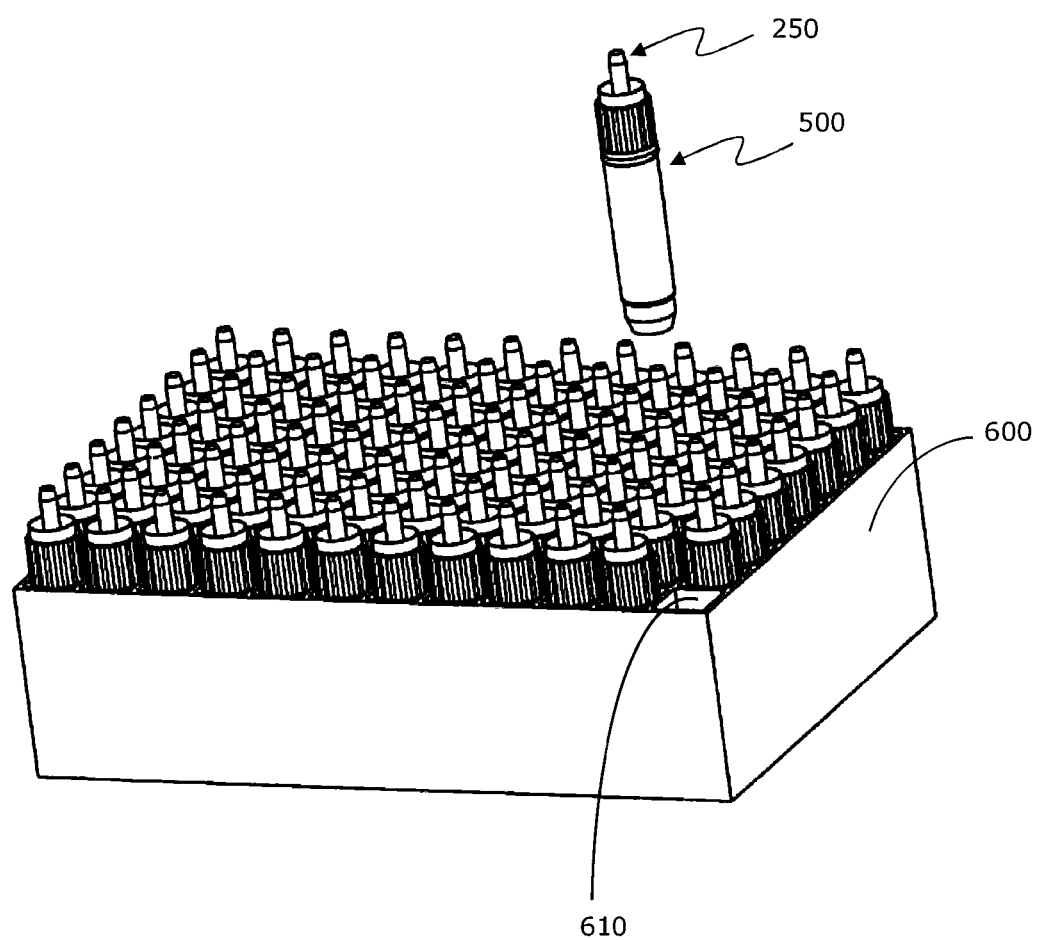
FIG. 24 is a perspective view of a plurality of collection devices held within a multi-cell rack.
Figure 26:
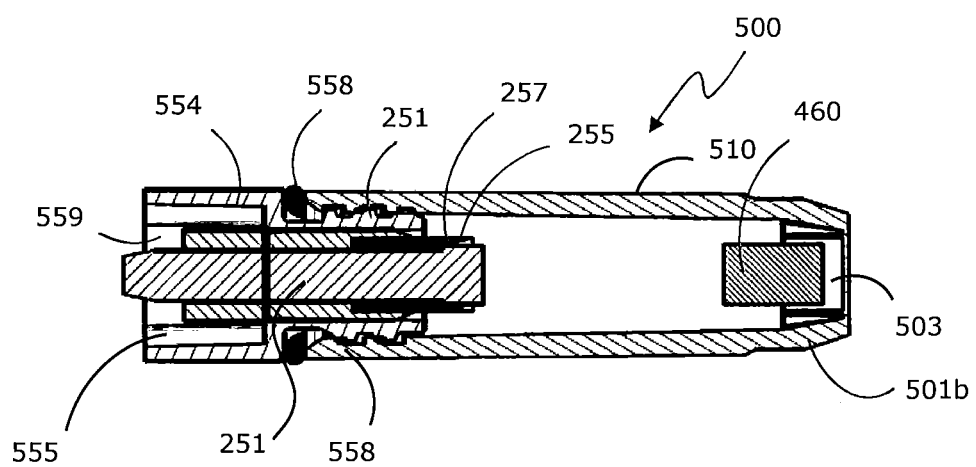
FIG. 26 is a cross-sectional side view of another form of storage tube in which the tissue sample is held in the tissue chamber of the tube.

Preferably, the tissue sample is held within the sample holding cavity when the storage tube is removed from the tissue sampler. The storage tubes may then be placed within respective cells of a multi-cell rack so that the base of each tube is at the bottom of the respective cell and the caps of the tubes project above the cells, as shown in FIG. 24. The diameter or width of the cells is sized to be commensurate with the diameter or width of the tubes.

A machine is typically used to depress the plungers within the caps of the tubes automatically, either by depressing the plunger of each tube consecutively or by simultaneously depressing the plungers of all tubes in the rack. As each plunger is depressed and pushed through the bore of the punch and through the sample holding cavity of the cutting element toward the base of the storage tube, the sample is pushed out of the sample holding cavity and is deposited into the chamber at the bottom of the tube, as shown in FIGS. 25a to 25d and FIG. 26.

Where the outer surface of the body of each tube comprises anti-rotation means, the tubes are located within the respective cells of the tube holder so that the anti-rotation means engage with corresponding anti-rotation means provided within the cells. For example, one or more projections formed on a tube body will engage with one or more recesses formed in the walls of the respective cell. The anti-rotation means of the tubes and cells prevent the tubes from rotating within the cells so that the tubes can be automatically decapped by unscrewing the caps from the tubes.

To decap the tubes, a cap engaging tool (not shown) engages with the correspondingly shaped recess of the cap, or to grip onto the outer surface of the guide wall of the cap, and is rotated in the appropriate direction to unscrew the cap from the tube. Typically, a machine is provided in which multiple cap engaging tools engage with the caps of multiple tubes in a rack to decap the tubes of the rack simultaneously, as shown in FIGS. 27, 28a to 28c. Decapping the tubes enables the samples within the tubes to be accessed and removed from the tubes for analysis.

Optionally, the base of each storage tube and/or the rack may be adapted to provide a tube lock feature in which the tube is locked in place within a respective cell. The tube may locked within the cell in any suitable arrangement. For example, the exterior of the tube may be threaded to engage with a threaded interior of the cell or the tube may be adapted to snugly fit or snap-fit into a cell of a rack. Once the tube is locked within the cell, the tube is held in place even if the rack is inverted. By using this feature, the rack can be inverted to eject the samples from the tubes.

Optionally, each cell within the rack comprises an open or transparent bottom for reading unique indicia located on the base of each tube held within the rack so that the source of each sample can be identified and linked with the data obtained from the sample.

Although no tagging operation has been described in relation to the use of the tissue sampler described above, it is envisaged that a tagging operation could be conducted simultaneously with, or sequential, to the tissue sampling operation.

Advantages

The tissue sampler of the invention enables multiple tissue samples to be collected efficiently by avoiding the need to load a fresh punch into the tissue sampler after each sample is collected. Furthermore, the tissue sampler avoids the need for the user to handle and/or dispose of used punches. Another advantage offered by the tissue sampler of the invention is that the quick release mechanism, provided by the over-centre linkage, actuation rod compression spring, and striker, makes it less likely that an animal could react to the cutting operation and pull the tissue sampler from the user's hand, which causes more stress and potential damage to the animal and can make it difficult for the user to retrieve the tissue sampler.

An advantage of the collecting device of the invention is that both the punch and plunger are held within the storage tube after a sample is taken, so it is not necessary for the user to handle and/or dispose of the used punch. Furthermore, the collecting device allows for the sample to be held within a sample holding cavity of the device and to be deliberately ejected from the cavity and into a storage tube.

The storage tube of the invention also offers the advantage that the tube can be hermetically sealed and is optionally tamper evident.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

What we claim is:

1. A kit of parts comprising
    a storage tube for storing a tissue sample therein comprising
    i) a tube body having an open first end, a closed second end, and
    ii) a cap at the open first end of the tube body, the cap being removable from the tube body and having a breakable seal that extends across the tube body to seal the open first end of the tube body,
    a collecting device for collecting the tissue sample and delivering the tissue sample into the storage tube, the collecting device comprising;
    a) a punch having a cutting element with a cutting edge formed at a cutting end of the punch and also comprising a centrally located bore that extends through the punch and cutting element, wherein the cutting element extends from and surrounds one end of the bore at the cutting end of the punch to form a surrounding wall within which a cavity to hold the tissue sample is defined, the punch having a pushing end opposite the cutting end at where the punch can be pushed to pass through part of an animal from which the tissue sample is to be removed to collect the tissue sample, wherein the cutting edge is configured to break the breakable seal of the cap to form an opening through the cap to the tube body and wherein the collecting device is configured to be held within the opening in the cap of the storage tube to close off the open first end of the tube body and so that the collecting device is removed with the removal of the cap from the tube body,
    b) a plunger located within the bore of the punch and configured to slide within the bore so that a first end of the plunger can slide toward the cutting edge of the punch and a second end of the plunger opposite the first end of the plunger projects out of the cavity and from the pushing end of the punch and out of the cap when the collecting device is held within the cap and the tissue sample is in the cavity so that the second end of the plunger can be pushed towards the cavity to cause the first end of the plunger to push the tissue sample out of the cavity.

2. The kit of parts of claim 1, wherein the breakable seal is in the form of a membrane.

3. The kit of parts of claim 1, wherein the first end of the plunger is enlarged.

4. The kit of parts of claim 1, wherein a surface of the first end of the plunger comprises a non-stick material.

5. The kit of parts of claim 1, wherein the plunger comprises an RFID device.

6. A method of decapping a storage tube comprising a tube body having an open first end, a closed second end, and a removable cap attached to the open first end of the tube body, wherein a collecting device is located within an opening formed in the cap and acts to close off the open first end of the tube body, the collecting device comprising a punch having:

i) a cutting element with a cutting edge formed at a cutting end of the punch;
ii) a pushing end of the punch located opposite the cutting end of the punch; and
iii) a centrally located bore that extends through the punch and cutting element, wherein the cutting element surrounds one end of the bore at the cutting end of the punch to form a surrounding wall defining a cavity that holds a tissue sample, a plunger located within the bore of the punch and configured to slide within the bore so that a first end of the plunger can slide toward the cutting edge of the punch and a second end of the plunger opposite the first end of the plunger projects out of the cavity and from the pushing end of the punch and out of the cap when the collecting device is held within the cap and the tissue sample is in the cavity so that the second end of the plunger can be pushed towards the cavity to cause the first end of the plunger to push the tissue sample out of the cavity, the method comprising the steps of:

(a) depressing the second end of the plunger toward the pushing end of the punch to cause the first end of the plunger to push the tissue sample out of the cavity and into the tube body; and (b) removing the cap, including the collecting device held therein, from the tube body to access the tissue sample within the tube body.

7. The method of claim 6, wherein the storage tube is one of a plurality of storage tubes, each storage tube being held within a cell of a multi-cell rack.

8. The method of claim 7, wherein each of the plurality of storage tubes are decapped simultaneously by a decapping machine, the decapping machine comprising multiple cap engaging tools to engage with the caps of the plurality of storage tubes.

* * * * *